US011013797B2

(12) United States Patent
Sato et al.

(10) Patent No.: US 11,013,797 B2
(45) Date of Patent: May 25, 2021

(54) PORCINE EPIDEMIC DIARRHEA PREVENTATIVE OR THERAPEUTIC METHOD, VACCINE, AND VACCINE KIT

(71) Applicants: NIPPON INSTITUTE FOR BIOLOGICAL SCIENCE, Ome (JP); NISSEIKEN CO., LTD., Ome (JP)

(72) Inventors: Tetsuo Sato, Ome (JP); Kazuki Oroku, Ome (JP); Yoshiyuki Ohshima, Ome (JP); Yoshiaki Furuya, Ome (JP); Nobuyuki Tsutsumi, Ome (JP)

(73) Assignees: NIPPON INSTITUTE FOR BIOLOGICAL SCIENCE, Ome (JP); NISSEIKEN CO., LTD., Ome (JP)

(\*) Notice: Subject to any disclaimer, the term of this patent is extended or adjusted under 35 U.S.C. 154(b) by 0 days.

(21) Appl. No.: 16/325,615

(22) PCT Filed: Jul. 24, 2017

(86) PCT No.: PCT/JP2017/026692
§ 371 (c)(1),
(2) Date: Feb. 14, 2019

(87) PCT Pub. No.: WO2018/034106
PCT Pub. Date: Feb. 22, 2018

(65) Prior Publication Data
US 2019/0209676 A1 Jul. 11, 2019

(30) Foreign Application Priority Data
Aug. 17, 2016 (JP) .............................. JP2016-159797

(51) Int. Cl.
*A61K 39/225* (2006.01)
*A61K 39/39* (2006.01)
*A61P 31/12* (2006.01)
*A61K 9/00* (2006.01)
*A61K 39/00* (2006.01)

(52) U.S. Cl.
CPC .......... *A61K 39/225* (2013.01); *A61K 9/0019* (2013.01); *A61K 9/0043* (2013.01); *A61K 39/39* (2013.01); *A61P 31/12* (2018.01); *A61K 2039/5254* (2013.01); *A61K 2039/54* (2013.01); *A61K 2039/545* (2013.01); *A61K 2039/552* (2013.01); *A61K 2039/555* (2013.01)

(58) Field of Classification Search
CPC .. A61K 39/225; A61K 9/0019; A61K 9/0043; A61K 39/39; A61K 2039/5254; A61K 2039/54; A61K 2039/545; A61K 2039/552; A61K 2039/555; A61K 2039/55566; A61K 2039/5252; A61K 39/215; A61K 39/12; A61K 2039/543; A61K 2039/542; A61P 31/12; A61P 31/14; C12N 2770/20034
See application file for complete search history.

(56) References Cited

U.S. PATENT DOCUMENTS

| 2004/0081654 A1 | 4/2004 | Schryvers et al. |
| 2004/0258701 A1\* | 12/2004 | Dominowski ....... A61K 9/1075 424/184.1 |
| 2015/0283229 A1 | 10/2015 | Hernandez et al. |

FOREIGN PATENT DOCUMENTS

| CN | 104667269 | | 6/2015 | |
| JP | 10-218788 | | 8/1998 | |
| JP | 2004-513879 | | 5/2004 | |
| KR | 101442493 B1 | \* | 9/2014 | |
| KR | 101654023 B1 | \* | 9/2016 | ............. A61K 39/12 |
| KR | 20170030175 A | \* | 3/2017 | |
| WO | 2015153425 | | 10/2015 | |
| WO | WO-2016007576 A2 | \* | 1/2016 | ............. A61K 39/12 |

OTHER PUBLICATIONS

Lu S. Heterologous prime-boost vaccination. Curr Opin Immunol. Jun. 2009;21(3):346-51. doi: 10.1016/j.coi.2009.05.016. Epub Jun. 6, 2009.\*
Guo X, Deng Y, Chen H, Lan J, Wang W, Zou X, et. al. Systemic and mucosal immunity in mice elicited by a single immunization with human adenovirus type 5 or 41 vector-based vaccines carrying the spike protein of Middle East respiratory syndrome coronavirus. Immunology. Aug. 2015;145(4):476-84. Epub Apr. 21, 2015.\*
Saif LJ. Lactogenic immunity and vaccines for Porcine Epidemic Diarrhea Virus (PEDV): Lessons from Transmissible Gastroenteritis Virus (TGEV) trials and tribulations. 2014 North American PRRS Symposium, Dec. 5-6, Chicago, Illinois, USA. p. 36, Abstract 14.\*
Meeusen EN, Walker J, Peters A, Pastoret PP, Jungersen G. Current status of veterinary vaccines. Clin Microbiol Rev. Jul. 2007;20(3):489-510, table of contents.\*
Hou Y, Wang Q. Emerging Highly Virulent Porcine Epidemic Diarrhea Virus: Molecular Mechanisms of Attenuation and Rational Design of Live Attenuated Vaccines. Int J Mol Sci. Nov. 4, 2019;20(21):5478.\*
Mlsset Uitgeverij B.V. "Pig Progress: Porcine Epidemic Diarrhoea (PED)" Accessed May 22, 2020, https://www.pigprogress.net/Health/Health-Tool/diseases/Porcine-Epidemic-Diarrhoea-PED/).\*
Pascual-Iglesias A, Sanchez CM, Penzes Z, Sola I, Enjuanes L, Zuñiga S. Recombinant Chimeric Transmissible Gastroenteritis Virus (TGEV)—Porcine Epidemic Diarrhea Virus (PEDV) Virus Provides Protection against Virulent PEDV. Viruses. Jul. 25, 2019;11(8):682.\*

(Continued)

*Primary Examiner* — Rachel B Gill
(74) *Attorney, Agent, or Firm* — Carmody Torrance Sandak & Hennessey LLP

(57) ABSTRACT

A method for preventing or treating porcine epidemic diarrhea, the method including: administering a live vaccine of a porcine epidemic diarrhea virus and an adjuvant to a pig through oral administration or nasal administration; and administering an inactivated vaccine of the porcine epidemic diarrhea virus and an adjuvant to the pig through intramuscular administration.

3 Claims, 1 Drawing Sheet
Specification includes a Sequence Listing.

(56) References Cited

OTHER PUBLICATIONS

Shah RR, Taccone M, Monaci E, Brito LA, Bonci A, O'Hagan DT, Amiji MM, Seubert A. The droplet size of emulsion adjuvants has significant impact on their potency, due to differences in immune cell-recruitment and -activation. Sci Rep. Aug. 8, 2019;9(1):11520.*

Pellegrino P, Clementi E, Radice S. On vaccine's adjuvants and autoimmunity: Current evidence and future perspectives. Autoimmun Rev. Oct. 2015;14(10):880-8. doi: 10.1016/j.autrev.2015.05.014. Epub May 29, 2015.*

Del Giudice G, Rappuoli R, Didierlaurent AM. Correlates of adjuvanticity: A review on adjuvants in licensed vaccines. Semin Immunol. Oct. 2018;39:14-21. Epub May 23, 2018.*

Delrue I, Verzele D, Madder A, Nauwynck HJ. Inactivated virus vaccines from chemistry to prophylaxis: merits, risks and challenges . Expert Rev Vaccines. Jun. 2012;11(6):695-719.*

Lee C. Porcine epidemic diarrhea virus: An emerging and re-emerging epizootic swine virus. Virol J. Dec. 22, 2015; 12:193. Erratum in: Virol J. 2016;13:19.*

Chen F, Zhu Y, Wu M, Ku X, Ye S, Li Z, Guo X, He Q. Comparative Genomic Analysis of Classical and Variant Virulent Parental/Attenuated Strains of Porcine Epidemic Diarrhea Virus. Viruses. Oct. 23, 2015;7(10):5525-38.*

Wang J, Zhao P, Guo L, Liu Y, Du Y, Ren S, et al. Porcine Epidemic Diarrhea Virus Variants with High Pathogenicity, China. Emerg Infect Dis. 2013;19(12):2048-2049.*

Li W, Li H, Liu Y, Pan Y, Deng F, Song Y, Tang X, He Q. New variants of porcine epidemic diarrhea virus, China, 2011. Emerg Infect Dis. Aug. 2012;18(8):1350-3.*

Sato T, Takeyama N, Katsumata A, Tuchiya K, Kodama T, Kusanagi K. Mutations in the spike gene of porcine epidemic diarrhea virus associated with growth adaptation in vitro and attenuation of virulence in vivo. Virus Genes. Aug. 2011;43(1):72-8. Epub May 11, 2011.*

Oka T, Saif LJ, Marthaler D, Esseili MA, Meulia T, et. al. Cell culture isolation and sequence analysis of genetically diverse US porcine epidemic diarrhea virus strains including a novel strain with a large deletion in the spike gene. Vet Microbiol. Oct. 10, 2014; 173(3-4):258-69. Epub Aug. 27, 2014.*

Song DS, Yang JS, Oh JS, Han JH, Park BK. Differentiation of a Vero cell adapted porcine epidemic diarrhea virus from Korean field strains by restriction fragment length polymorphism analysis of ORF 3. Vaccine. May 16, 2003;21(17-18): 1833-42. (Year: 2003).*

Zimmerman, et al., "Diseases of Swine," Wiley-Blackwell, 10th Edition, pp. 514-524, 2012.

Lee, C., "Porcine epidemic diarrhea virus: An emerging and re-emerging epizootic swine virus," Virology Journal, vol. 12:193, pp. 1-16, Dec. 22, 2015.

Sueyoshi, et al., "An Immunohistochemical Investigation of Porcine Epidemic Diarrhoea," J. Comp. Path., vol. 113, pp. 59-67, Mar. 10, 1995.

Miyazaki, A., "Regarding recently prevailed porcine epidemic diarrhea (PED)," The Journal of Veterinary Epidemiology, vol. 18, No. 1, pp. 85-89, 2014.

Sato, T., "Characteristics and effects of porcine epidemic diarrhea live vaccine," Pig Journal, pp. 22-25, Feb. 2014.

Song, et al., "Porcine epidemic diarrhea: a review of current epidemiology and available vaccines," Clin. Exp. Vaccine Res., vol. 4, No. 2, pp. 166-176, Jun. 25, 2015.

Song, et al., "Oral efficacy of Vero cell attenuated porcine epidemic diarrhea virus DR13 strain," Research in Veterinary Science, vol. 82, pp. 134-140, Mar. 27, 2006.

Shiga, A., "The countermeasure and the effect in the swine farm-D where a porcine epidemic diarrhea infection occured at a farrowing house for the first time," Proceedings of the Japanese Pig Veterinary Society, No. 67, pp. 18-20, Feb. 1, 2016.

Chattha, et al., "Strategies for Design and Application of Enteric Viral Vaccines," Annu. Rev. Anim. Biosci., vol. 6, pp. 375-395, Oct. 6, 2014.

Sato, T., "Current status and future prospects of porcine epidemic diarrhea live vaccine," All about Swine, vol. 49, pp. 13-21, Sep. 2016.

Japanese Patent Office, First Office Action in corresponding Japanese patent application No. 2016-159797, dated Sep. 12, 2017.

European Patent Office, Extended European Search Report issued in corresponding Application No. EP17841334.0, dated Apr. 2, 2020.

Paudel., S. et al., "Evaluation of antibody response of killed and live vaccines against porcine epidemic diarrhea virus in a field study," Veterinary Quarterly, vol. 34, No. 4, pp. 194-200, Oct. 2, 2014.

Jang, S.I. et al., "Montanide IMS 1313 N VG PR nanoparticle adjuvant enhances antigen-specific immune responses to profilin following mucosal vaccination against Eimeria acervulina," Veterinary Parasitology, vol. 182, No. 2, May 16, 2011.

Sato, T. et al., "Efficacy of genogroup 1 based porcine epidemic diarrhea live vaccine against genogroup 2 field strain in Japan," Virology Journal, vol. 15, No. 1, Feb. 2, 2018.

Saif, L.J., et al., Coronaviruses, Diseases of Swine, Tenth Edition, Chapter 35, 2012, pp. 501-524.

Lin, C-M., et al., Antigenic Relationships Among Porcine Epidemic Diarrhea Virus and Transmissible Gastroenteritis Virus Strains, Journal of Virology, vol. 89, No. 6, Mar. 2015, pp. 3332-3342.

Taiwanese Patent Office, Office Action issued in Taiwanese Application No. 106125846 dated Nov. 12, 2020.

LV, Chaochao, et al. "Porcine epidemic diarrhea virus: current insights." Virus Adaptation and Treatment 2016:8 pp. 1-12.

* cited by examiner

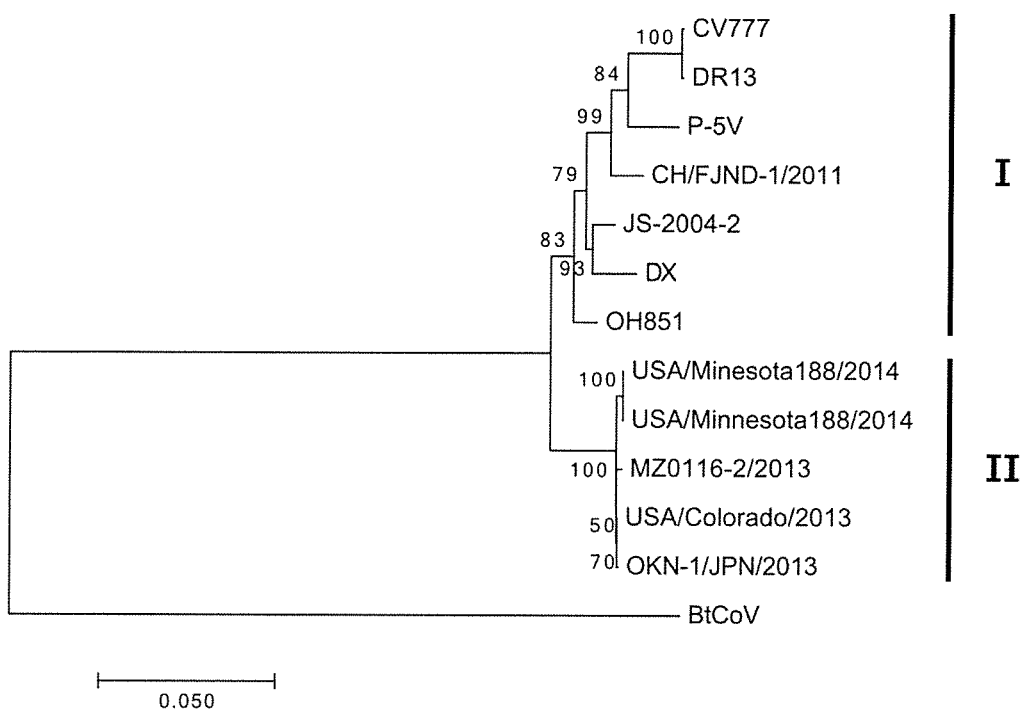

PORCINE EPIDEMIC DIARRHEA PREVENTATIVE OR THERAPEUTIC METHOD, VACCINE, AND VACCINE KIT

TECHNICAL FIELD

The present invention relates to a method for preventing or treating porcine epidemic diarrhea, a vaccine for oral or nasal administration, a vaccine for intramuscular administration, and a vaccine kit.

BACKGROUND ART

Porcine epidemic diarrhea: PED is caused through oral infection of PED virus (PEDV) contained in feces of an infected pig and is mainly characterized by watery diarrhea and anorexia. The porcine epidemic diarrhea is a viral infectious disease exhibiting a considerably high fatality rate in suckling pigs aged 1 week or less (see NPL 1). There has been a problem that once PEDVs enter a hog raising farm, it is difficult to remove the PEDVs, resulting in severe economic damage. The porcine epidemic diarrhea has prevailed in recent years in Asian countries and Northern American continent such as America, resulting in severe economic damage (see NPL 2).

Target cells of the PEDVs are epithelial cells of the gastrointestinal tracts, particularly the intestinal jejunum and the intestinal ileum (see NPL 3). It is considered that some of the PEDVs enter the blood flow through the lymphoid tissue under the mucosas, and there is also a period at which the PEDV genes are detected in the organs throughout the whole body. However, the PEDVs do not exhibit a secondary replication in other organs. Therefore, after the PEDVs are replicated in the gastrointestinal epithelial cells, and the feces are excreted, generating a new source of infection. Pigs after the weaning stage are decreased in sensitivity to the PEDV and may live with subclinical even when the PEDVs are orally forcibly administered to the pigs. However, when the pigs under such a stress condition as infection of other pathogens, a delivery, or an overcrowding breeding are exposed to the PEDVs, they transiently develop symptoms such as anorexia and diarrhea in some cases (see NPL 4).

The vaccines for the porcine epidemic diarrhea (hereinafter may be referred to as "PED vaccine") have been available in Japan, South Korea, China, the Philippines, and America since the late 1990s. These conventional PED vaccines are designed based on the following mechanism. Specifically, these conventional PED vaccines are administered to sows during a pregnancy period, and then the neutralizing antibodies against the PEDVs are secreted in the milk of the sow after a delivery. When a suckling pig takes in this milk, the PEDVs entered in the gastrointestinal tract of the suckling pig are neutralized (see NPL 5). The suckling pig cannot be prevented from infection with the PEDV through only maternal antibodies contained in the colostrum. Throughout a period of suckling, the PEDVs can be neutralized by continuing to take in the milk that has a high concentration of the neutralizing antibodies against the PEDV by virtue of the PED vaccine. As a result, it is possible to prevent pathogenesis of the porcine epidemic diarrhea or alleviate its symptoms.

However, there is a problem that when a piglet is under such a condition that cannot take in the milk due to any reason, the piglet is infected with the PEDV, advancing in severe symptoms. Moreover, there are also problems that when a sow negative for the PEDV antibody and a sow possessing a low immune level are exposed to a large amount of the PEDVs, they will show systemic symptoms including a reduction in the lactation, and the effects of the PED vaccine cannot be sufficiently achieved.

There are also problems that the effects of the conventional PED vaccines are limited to a reduction in the symptoms caused by the PEDVs and reduction in mortality of the piglets and induction of the humoral immune response is insufficient, which cannot insufficiently induce the response of the IgA antibody (see NPL 6).

Accordingly, there are strong demands for provision of a new vaccine for the porcine epidemic diarrhea that not only enables production induction of the neutralizing antibody specific to the PEDV in the milk but also enables induction of immune response capable of preventing the sow itself from infection, and for provision of a method for preventing or treating porcine epidemic diarrhea.

CITATION LIST

Non-Patent Literatures

NPL 1: Zimmerman J. J. et al., Diseases of swine, 10th edition, Wiley-Blackwell 2012

NPL 2: Lee C., Virol J, 2015, Vol. 12, p. 193

NPL 3: Sueyoshi M. et al., J. Comp. Pathol, 1995, Vol. 113 (1), pp. 59-67

NPL 4: Ayako Miyazaki, "Regarding recently prevailed porcine epidemic diarrhea (PED)", The Journal of Veterinary Epidemiology, 2014, 18 (1), pp. 85-89

NPL 5: Tetsuo Sato, "Characteristics and effects of porcine epidemic diarrhea live vaccine", PIG JOURNAL, 2014, February, pp. 22-25

NPL 6: Song D. et al., Clin. Exp. Vaccine Res., 2015, Vol.4 (2), pp. 166-176

SUMMARY OF INVENTION

Technical Problem

An object of the present invention is to solve the conventionally existing problems and to achieve the following objects. That is, an object of the present invention is to provide a method for preventing or treating porcine epidemic diarrhea, a vaccine kit, a vaccine for oral or nasal administration, and a vaccine for intramuscular administration, which are excellent in production induction activity of the neutralizing antibody specific to the porcine epidemic diarrhea virus and induction activity of the humoral immune response, and can efficiently prevent or treat the porcine epidemic diarrhea.

Solution to Problem

As a result of the studies diligently performed by the present inventors to achieve the aforementioned object, it was found that when a live vaccine of a porcine epidemic diarrhea virus and an adjuvant are administered to a pig through oral administration or a nasal administration, and then an inactivated vaccine of the porcine epidemic diarrhea virus and an adjuvant are further administered through intramuscular administration, it is possible not only to enhance production induction of the neutralizing antibody specific to the porcine epidemic diarrhea virus but also to induce the IgA antibody specific to the porcine epidemic diarrhea virus, compared to the conventional vaccines for the porcine epidemic diarrhea. Moreover, it was found that these antibodies are secreted in the milk and make it possible not only to prevent piglets from being infected but also to prevent sows themselves from being infected.

The present invention is based on the finding by the present inventors. Means for solving the aforementioned object are as follows. That is, <1> A method for preventing or treating porcine epidemic diarrhea, the method including:

administering a live vaccine of a porcine epidemic diarrhea virus and an adjuvant to a pig through oral administration or nasal administration; and administering an inactivated vaccine of the porcine epidemic diarrhea virus and an adjuvant to the pig through intramuscular administration.

<2> A vaccine kit including:

a live vaccine of a porcine epidemic diarrhea virus for oral or nasal administration;

an adjuvant for oral or nasal administration;

an inactivated vaccine of the porcine epidemic diarrhea virus for intramuscular administration; and an adjuvant for intramuscular administration.

<3> A vaccine for oral or nasal administration, the vaccine including:

a live vaccine of a porcine epidemic diarrhea virus; and an adjuvant, wherein the vaccine is used for a pig which is subsequently given booster immunization through intramuscular administration of an inactivated vaccine of the porcine epidemic diarrhea virus and an adjuvant.

<4> A vaccine for intramuscular administration, the vaccine including:

an inactivated vaccine of a porcine epidemic diarrhea virus; and an adjuvant, wherein the vaccine is used for a pig which has been given priming immunization through oral administration or nasal administration of a live vaccine of the porcine epidemic diarrhea virus and an adjuvant.

Advantageous Effects of Invention

According to the present invention, it is possible to solve the conventionally excising problems, achieve the object, and provide a method for preventing or treating porcine epidemic diarrhea, a vaccine kit, a vaccine for oral or nasal administration, and a vaccine for intramuscular administration, which are excellent in production induction activity of the neutralizing antibody specific to the porcine epidemic diarrhea virus and induction activity of the humoral immune response, and can efficiently prevent or treat the porcine epidemic diarrhea.

BRIEF DESCRIPTION OF DRAWINGS

FIG. 1 is a diagram presenting a result of phylogenetic analysis of a PEDV spike gene.

DESCRIPTION OF EMBODIMENTS (Method for Preventing or Treating Porcine Epidemic Diarrhea)

A method of the present invention for preventing or treating porcine epidemic diarrhea includes a first administration step and a second administration step and further includes other steps if necessary.

<First Administration Step>

The first administration step is a step of administering a live vaccine of a porcine epidemic diarrhea virus and an adjuvant to a pig through oral administration or nasal administration.

<<Live Vaccine of Porcine Epidemic Diarrhea Virus (PEDV)>>

The live vaccine of PEDV is a vaccine obtained by attenuating toxicity of the PEDV.

The PEDV is a virus belonging to Coronaviridae, *Alphacoronavirus*, and is classified into two genetic groups of Group I and Group II.

Classification of the PEDV used for the live vaccine of PEDV is not particularly limited and may be appropriately selected depending on the intended purpose. The classification thereof may be the above Group I or Group II. These PEDVs may be used alone or in combination.

A method for obtaining the PEDV is not particularly limited and may be appropriately selected depending on the intended purpose. Examples thereof include a method for obtaining the PEDV by isolating it from a pig that has been infected with the PEDV and a method using a commercially available product.

One specific example of the method for obtaining the PEDV by isolating the PEDV from a pig that has been infected with the PEDV is, for example, the following method.

The small intestine is collected from a pig that has developed the porcine epidemic diarrhea (PED), and a tissue homogenate is prepared. Then, the tissue homogenate is orally administered to a pig that has not been infected with the PED. After several days, the small intestine of this pig is collected and is used for preparing a tissue homogenate. Such passages are performed for the number of times that is appropriately selected. Then, trypsin is added to a tissue homogenate obtained at the last generation so as to be a final concentration of 5 µg/mL to 10 µg/mL. Then, the resultant is inoculated into Vero cells that have been made confluent and is cultured in a 5 µg/mL to 10 µg/mL trypsin-added culture medium. The cytopathic effect (CPE) is confirmed every day using an optical microscope. At a point of time when the CPE is observed, the culture is terminated. From a culture supernatant of the Vero cells in which the CPE has been confirmed, the RNA is extracted through a routine method, and primer sequences set forth in SEQ ID NOs: 1 to 16 are used to perform the RT-PCR. Then, the amplified RT-PCR product is subjected to cloning in any vector through a routine method to obtain a plasmid thereby. A nucleotide sequence of a PEDV spike gene (hereinafter may be referred to as "PEDV S gene") in the plasmid is analyzed through a routine method. Then, the respective sequence fragments analyzed are assembled. For example, by performing the phylogenetic analysis through the neighbor-joining method with MEGA 4.0 software, it is possible to judge whether the subject is the PEDV belonging to the Group I or the PEDV belonging to the Group II in the genetic group.

One specific example of the method using a commercially available product is a method by inoculating a commercially available live vaccine into Vero cells and then culturing the cells. In this case, a culture medium to which trypsin is not added is preferably used.

Examples of the PEDV belonging to the Group I include P-5V strain (Sato T. et al., Virus Genes, 2011, Vol. 43 (1), pp. 72-78), CV777 strain (Pensaert M. B. et al., Arch. Virol., 1978, Vol. 58 (3), pp. 243-247), DR13 strain (Park S. J. et al., Virus Genes, 2007, Vol 35 (1), pp. 55-64), 96-P4C6 strain (The Chemo-Sero-Therapeutic Research Institute, SUIMMUGEN Registered Trademark TGE/PED vaccine strain), JS-2004-2 strain (Zhao P. D. et al., Can. J. Vet. Res., 2015, Vol. 79 (1), 8-15), OH851 strain (Wang L. et al., Emerg. Infect. Dis., 2014, Vol. 20 (5), pp. 917-919), CH/FJND-1/2011 strain (Tian Y., et al., Viruses, 2013, Vol. 5 (8), pp. 1991-2004), and DX strain (Zhao P. D. et al., Can. J. Vet. Res., 2015, Vol. 79 (1), 8-15).

The P-5V strain can be easily cultured from NISSEIKEN PED Vaccine (live) (available from Nisseiken Co., Ltd) through the aforementioned method.

Examples of the PEDV belonging to the Group II include MZ0116-2/2013 strain (see the below-described "Test Example 2"), OKN-1/JPN/2013 strain (Suzuki T. et al., Infect. Genet. Evol. 2015, Vol. 36, pp. 363-368), USA/Colorado/2013 strain (Marthaler D. et. al., Genome Announce., 2013, Vol. 1 (4), pp. e00555-13), and USA/Minnesota188/2014 strain (Marthaler D. et al., Emerg. Infect. Dis., 2014, Vol. 20 (12), pp. 2162-2163).

The method for attenuating pathogenicity of the PEDV is not particularly limited and may be appropriately selected from known methods depending on the intended purpose. One example of the method is, for example, a method by subculturing the PEDVs in heterologous hosts.

The heterologous hosts are not particularly limited and may be appropriately selected depending on the intended purpose. Examples thereof include culture cells and embryonated eggs.

A dose of the live vaccine of PEDV in the first administration step is not particularly limited and may be appropriately selected depending on the various factors such as age, body weight, physical constitution, and symptom of an individual to be administered, and presence or absence of administration of a medicine or a drug containing other ingredients as an active ingredient. The dose is preferably such a dose that a virus content per one administration is $10^{7.0}$ $TCID_{50}$ or more ($10^{7.0}$ $TCID_{50}$/dose or more). When the dose is less than $10^{7.0}$ $TCID_{50}$/dose, production of the neutralizing antibody specific to the PEDV and induction of the humoral immune response cannot be achieved. As a result, the porcine epidemic diarrhea cannot be prevented or treated in some cases.

<<Adjuvant>>

The kind of the adjuvant is not particularly limited and may be appropriately selected depending on the intended purpose. Examples thereof include aluminum salts, complete Freund's adjuvants, Freund's incomplete adjuvants, saponin, Monophosphoryl lipid A: MPL, microemulsion adjuvants, cholera toxins, E. coli heat-labile enterotoxins, CpG oligonucleotide, polyinosinic-polycytidylic acid (poly (I:C)), polymer adjuvants, squalene, dextrin derivatives, liquid paraffin, tocopherol acetate, and polysorbate. The adjuvant may be used alone or in combination.

Among them, microemulsion adjuvants, cholera toxins, E. coli heat-labile enterotoxins, CpG oligonucleotide, polyinosinic-polycytidylic acid (poly (I:C)), polymer adjuvants, and squalene are preferable, microemulsion adjuvants are particularly preferable.

The microemulsion adjuvant is formed of fine oily particles dispersed in water. The fine oily particles are those obtained by mixing a light mineral oil and a surfactant and then emulsifying them in water and have particles of 5 nm to 500 nm.

The light mineral oil is not particularly limited and may be appropriately selected depending on the intended purpose. Examples thereof include liquid paraffin, etherified liquid paraffin, and light liquid paraffin (Japanese Pharmacopoeia). These light mineral oils may be used alone or in combination.

Examples of the liquid paraffin include MARCOL (Trademark) 52 (product name, available from Exxon Mobil) and Penreco (Registered Trademark) Drakeol (Registered Trademark) 6VR (product name, available from Penreco).

The content of the light mineral oil in the microemulsion adjuvant is not particularly limited and may be appropriately selected depending on the intended purpose. The content thereof is preferably 0.001% by mass to 10.0% by mass, more preferably 0.01% by mass to 0.1% by mass. When the content of the light mineral oil is less than 0.001% by mass, the particles may be unstable. When the content thereof is more than 10.0% by mass, the residue of the vaccinated product may remain in an animal to be vaccinated.

The surfactant is not particularly limited and may be appropriately selected depending on the intended purpose. Examples thereof include mannide monooleic acid, ethoxylated derivatives of oleic acid mannitan ester, glyceryl monostearate, decaglyceryl monolaurate, Sorbitan monooleate, and polyoxyethylene (20) sorbitan monopalmitate. These surfactants may be used alone or in combination.

The content of the surfactant in the microemulsion adjuvant is not particularly limited and may be appropriately selected depending on the intended purpose, so long as the light mineral oil can be emulsified to form a microemulsion.

The microemulsion adjuvant may further contain a chelating agent. When the microemulsion adjuvant contains a chelating agent, antigens (PEDV) bonded to the fine oily particles are stabilized, or act of assisting the bond of the fine oily particles to immunocompetent cells is achieved, which is advantageous.

The chelating agent is not particularly limited and may be appropriately selected depending on the intended purpose. Examples thereof include polyionic acid complexes such as calcium gluconate, manganese gluconate, aluminum salicylate, and soluble aluminum acetates. These chelating agents may be used alone or in combination.

The content of the chelating agent in the microemulsion adjuvant is not particularly limited and may be appropriately selected depending on the intended purpose. The content thereof is preferably 0.002% by mass to 30% by mass, more preferably 0.01% by mass to 15% by mass. When the content of the chelating agent is less than 0.002% by mass, immune response activity cannot be enhanced in some cases. When the content of the chelating agent is more than 30% by mass, a side effect will be caused in a vaccinated animal in some cases.

A method for preparing the microemulsion adjuvant containing the chelating agent is not particularly limited and may be appropriately selected depending on the intended purpose. One exemplary method thereof is a method for preparing a microemulsion adjuvant by adding the light mineral oil, the surfactant, and the chelating agent to water, and emulsifying them with a known emulsification unit. Specifically, it is possible to use, for example, the methods described in Japanese Patent Application Laid-Open Nos. 20004-131417 and 2005-75752. In addition, as the microemulsion adjuvant, a commercially available product may be used. Examples of the commercially available product include IMS 1312 VG, IMS 1313 VG, IMS 251C, IMS 2215 VG, and IMS 3012 VG ST in the MONTANIDE IMS series (all products are available from SEPPIC).

The dose of the adjuvant in the first administration step is not particularly limited and may be appropriately selected depending on the various factors such as the kind of the adjuvant; presence or absence of administration of a medicine or a drug containing other ingredients as an active ingredient; and age, body weight, physical constitution, and symptom of an individual to be administered, so long as it does not compromise the effects of the live vaccine of PEDV.

The dose in the case where the adjuvant is the microemulsion adjuvant is not particularly limited. However, the dose is preferably such a dose that a volume ratio between the microemulsion adjuvant and a virus liquid containing the live vaccine of PEDV is 20/80 to 80/20, particularly preferably such a dose that the volume ratio is 50/50. When the volume ratio (microemulsion adjuvant/virus liquid containing the live vaccine of PEDV) is less than 20/80, production of the neutralizing antibody specific to the PEDV and induction of the humoral immune response cannot be achieved, and the porcine epidemic diarrhea cannot be prevented or treated in some cases. When the volume ratio is more than 80/20, swelling, induration, redness, pyrexia, and anaphylaxis shock will be caused on the administered portion, production of the neutralizing antibody specific to the PEDV and induction of the humoral immune response cannot be achieved, and the porcine epidemic diarrhea cannot be prevented or treated in some cases.

The timing at which the live vaccine of PEDV and the adjuvant are administered to a pig through oral administration or nasal administration is not particularly limited and may be appropriately selected depending on the intended purpose, so long as the adjuvant effects of the adjuvant can be achieved and the timing is before the second administration step. The live vaccine of PEDV and the adjuvant may be simultaneously administered or may be separately administered. However, simultaneous administration is preferable regarding simplicity.

A method for simultaneously administering the live vaccine of PEDV and the adjuvant to a pig through oral administration or nasal administration is not particularly limited and may be appropriately selected depending on the intended purpose. Examples thereof include a method by administering a composition obtained by mixing the live vaccine of PEDV and the adjuvant.

As the composition obtained by mixing the live vaccine of PEDV and the adjuvant, a vaccine of the present invention for oral or nasal administration, which will be described hereinafter, is suitably used.

When the live vaccine of PEDV and the adjuvant are separately administered to a pig through oral administration or nasal administration, the order of administration of the live vaccine of PEDV and the adjuvant is not particularly limited and may be appropriately selected depending on the intended purpose, so long as the adjuvant effects of the adjuvant can be achieved.

A dosage interval between the live vaccine of PEDV and the adjuvant is not particularly limited and may be appropriately selected depending on the intended purpose, so long as the adjuvant effects of the adjuvant can be achieved.

The number of times for which the first administration step is performed is not particularly limited and may be appropriately selected depending on the intended purpose. The present invention is advantageous in that one-time first administration step makes it possible to achieve sufficient effects.

<Second Administration Step>

The second administration step is a step of administering, through intramuscular administration, an inactivated vaccine of the porcine epidemic diarrhea virus and an adjuvant to a pig that has undergone the first administration step.

<<Inactivated Vaccine of Porcine Epidemic Diarrhea Virus (PEDV)>>

An inactivated vaccine of PEDV is a vaccine obtained by eliminating pathogenicity of the PEDV or attenuating its toxicity.

The classification and the acquisition method of the PEDV used for the inactivated vaccine of PEDV are not particularly limited and may be appropriately selected depending on the intended purpose. Examples thereof include the aspects described in the item of the live vaccine of PEDV in the first administration step.

A method for inactivating infectivity of the PEDV is not particularly limited and may be appropriately selected depending on the intended purpose from known methods. Examples thereof include a method by treating the PEDV with a drug such as formalin, a method by heating, a method by changing a pH, a method by emitting gamma rays, and a method by emitting ultraviolet rays.

As the PEDV used for the inactivated vaccine of PEDV, isolated viruses may be inactivated as they are, or the attenuated PEDV may be inactivated.

A dose of the inactivated vaccine of PEDV in the second administration step is not particularly limited and may be appropriately selected depending on the various factors such as age, body weight, physical constitution, and symptom of an individual to be administered, and presence or absence of administration of a medicine or a drug containing other ingredients as an active ingredient. The dose is preferably such a dose that a virus content per one administration is $10^{6.5}$ $TCID_{50}$ or more ($10^{6.5}$ $TCID_{50}$/dose or more), more preferably such a dose that the virus content per one administration is $10^{7.5}$ $TCID_{50}$ or more ($10^{7.5}$ $TCID_{50}$/dose or more). When the dose is less than $10^{6.5}$ $TCID_{50}$/dose, production of the neutralizing antibody specific to the PEDV and induction of the humoral immune response cannot be achieved. As a result, the porcine epidemic diarrhea cannot be prevented or treated in some cases.

<<Adjuvant>>

The kind of the adjuvant is not particularly limited and may be appropriately selected depending on the intended purpose. Examples thereof include those described in the item of the adjuvant in the first administration step.

Among them, for example, aluminum salts, microemulsion adjuvants, polymer adjuvants, dextrin derivatives, liquid paraffin, squalene, tocopherol acetate, and polysorbate are preferable, microemulsion adjuvants are particularly preferred.

An aspect of the microemulsion adjuvants is the same as described in the item of the adjuvant in the first administration step.

The dose of the adjuvant in the second administration step is not particularly limited and may be appropriately selected depending on the various factors such as the kind of the adjuvant; presence or absence of administration of a medicine or a drug containing other ingredients as an active ingredient; and age, body weight, physical constitution, and symptom of an individual to be administered, so long as it does not compromise the effects of the inactivated vaccine of PEDV.

The dose in the case where the adjuvant is the microemulsion adjuvant is not particularly limited. The dose is preferably such a dose that a volume ratio between the microemulsion adjuvant and a virus liquid containing the inactivated vaccine of PEDV is 20/80 to 80/20, particularly preferably such a dose that the volume ratio is 50/50. When the volume ratio (microemulsion adjuvant/virus liquid containing the inactivated vaccine of PEDV) is less than 20/80, production of the neutralizing antibody specific to the PEDV and induction of the humoral immune response cannot be achieved, and the porcine epidemic diarrhea cannot be prevented or treated in some cases. When the volume ratio is more than 80/20, swelling, induration, redness, pyrexia, and anaphylaxis shock will be caused on the administered portion, production of the neutralizing antibody specific to the PEDV and induction of the humoral immune response cannot be achieved, and the porcine epidemic diarrhea cannot be prevented or treated in some cases.

The timing at which the inactivated vaccine of PEDV and the adjuvant are administered to the pig through intramuscular administration is not particularly limited and may be appropriately selected depending on the intended purpose, so long as the adjuvant effects of the adjuvant can be achieved and the timing is after the first administration step. The inactivated vaccine of PEDV and the adjuvant may be simultaneously administered or may be separately administered. However, simultaneous administration is preferable regarding simplicity.

A method for simultaneously administering the inactivated vaccine of PEDV and the adjuvant to the pig through intramuscular administration is not particularly limited and may be appropriately selected depending on the intended purpose. Examples thereof include a method by administering a composition obtained by mixing the inactivated vaccine of PEDV and the adjuvant.

As the composition obtained by mixing the inactivated vaccine of PEDV and the adjuvant, a vaccine of the present invention for intramuscular administration, which will be described hereinafter, is suitably used.

When the inactivated vaccine of PEDV and the adjuvant are separately administered to the pig through intramuscular administration, the order of administration of the inactivated vaccine of PEDV and the adjuvant is not particularly limited and may be appropriately selected depending on the intended purpose, so long as the adjuvant effects of the adjuvant can be achieved.

A dosage interval between the inactivated vaccine of PEDV and the adjuvant is not particularly limited and may be appropriately selected depending on the intended purpose, so long as the adjuvant effects of the adjuvant can be achieved.

The number of times for which the second administration step is performed is not particularly limited and may be appropriately selected depending on the intended purpose. The present invention is advantageous in that one-time second administration step makes it possible to achieve sufficient effects.

A dosage interval between the first administration step and the second administration step is not particularly limited and may be appropriately selected depending on the intended purpose. The dosage interval is preferably 1 week to 20 weeks, more preferably 2 weeks to 10 weeks, particularly preferably 4 weeks to 10 weeks. When the dosage interval is less than 1 week, production of the neutralizing antibody specific to the PEDV and induction of the humoral immune response cannot be achieved, and the porcine epidemic diarrhea cannot be prevented or treated in some cases. Therefore, even after more than 20 weeks, production of the neutralizing antibody specific to the PEDV and induction of the humoral immune response cannot be achieved, and the porcine epidemic diarrhea cannot be prevented or treated in some cases.

(Vaccine Kit)

A vaccine kit of the present invention includes a live vaccine of a porcine epidemic diarrhea virus for oral or nasal administration, an adjuvant for oral or nasal administration, an inactivated vaccine of the porcine epidemic diarrhea virus for intramuscular administration, and an adjuvant for intramuscular administration, and further includes other constituents if necessary.

<Live Vaccine of Porcine Epidemic Diarrhea Virus (PEDV) for Oral or Nasal Administration>

The classification and the acquisition method of the PEDV used for the PEDV live vaccine for oral or nasal administration, and a method for attenuating pathogenicity of the PEDV are not particularly limited and may be appropriately selected depending on the intended purpose. Examples thereof include those described in the item of the live vaccine of PEDV in the first administration step in the method of the present invention for preventing or treating porcine epidemic diarrhea as described above.

The virus content of the PEDV live vaccine for oral or nasal administration in the vaccine kit is not particularly limited and may be appropriately selected depending on the number of times for use. The virus content of the PEDV live vaccine for oral or nasal administration per one administration is preferably $10^{7.0}$ $TCID_{50}$/dose or more. When the vaccine kit is used, the PEDV live vaccine for oral or nasal administration can be appropriately selected depending on the various factors such as age, body weight, physical constitution, and symptom of an individual to be administered, and presence or absence of administration of a medicine or a drug containing other ingredients as an active ingredient, and can be adjusted through dilution.

<Adjuvant for Oral or Nasal Administration>

The kind of the adjuvant for oral or nasal administration is not particularly limited and may be appropriately selected depending on the intended purpose. Examples thereof include those described in the item of the adjuvant in the first administration step of the method of the present invention for preventing or treating porcine epidemic diarrhea as described above.

Among them, microemulsion adjuvants, cholera toxins, *E. coli* heat-labile enterotoxins, CpG oligonucleotide, polyinosinic-polycytidylic acid (poly (I:C)), polymer adjuvants, and squalene are preferable, microemulsion adjuvants are particularly preferred.

An aspect of the microemulsion adjuvants is the same as described in the item of the adjuvant in the first administration step of the method of the present invention for preventing or treating porcine epidemic diarrhea as described above.

The content of the adjuvant for oral or nasal administration in the vaccine kit is not particularly limited and may be appropriately selected depending on, for example, the number of times for use and the content of a virus liquid containing the PEDV live vaccine for oral or nasal administration.

The vaccine kit may include the live vaccine of PEDV for oral or nasal administration and the adjuvant for oral or nasal administration, as individual constituents or in a state of a composition obtained by mixing them.

As the composition obtained by mixing the live vaccine of PEDV for oral or nasal administration and the adjuvant for oral or nasal administration, a vaccine of the present invention for oral or nasal administration, which will be described hereinafter, is suitably used.

<Inactivated Vaccine of Porcine Epidemic Diarrhea Virus (PEDV) for Intramuscular Administration>

The classification and the acquisition method of the PEDV used for the PEDV inactivated vaccine for intramuscular administration, and the method for inactivating infectivity of the PEDV are not particularly limited and may be appropriately selected depending on the intended purpose. Examples thereof include aspects described in the item of the inactivated vaccine of PEDV in the second administration step of the method of the present invention for preventing or treating porcine epidemic diarrhea as described above.

The virus content of the PEDV inactivated vaccine for intramuscular administration in the vaccine kit is not particularly limited and may be appropriately selected depending on the number of times for use. The virus content of the PEDV inactivated vaccine for intramuscular administration per one administration is preferably $10^{6.5}$ TCID$_{50}$/dose or more, more preferably $10^{7.5}$ TCID$_{50}$/dose or more. When the vaccine kit is used, the PEDV inactivated vaccine for intramuscular administration can be appropriately selected depending on the various factors such as age, body weight, physical constitution, and symptom of an individual to be administered, and presence or absence of administration of a medicine or a drug containing other ingredients as an active ingredient, and can be adjusted through dilution.

<Adjuvant for Intramuscular Administration>

The kind of the adjuvant for intramuscular administration is not particularly limited and may be appropriately selected depending on the intended purpose. Examples thereof include those described in the item of the adjuvant in the first administration step of the method of the present invention for preventing or treating porcine epidemic diarrhea as described above.

Among them, aluminum salts, microemulsion adjuvants, polymer adjuvants, dextrin derivatives, liquid paraffin, squalene, tocopherol acetate, and polysorbate are preferable, microemulsion adjuvants are particularly preferable.

An aspect of the microemulsion adjuvants is the same as described in the item of the adjuvant in the first administration step of the method of the present invention for preventing or treating porcine epidemic diarrhea as described above.

The content of the adjuvant for intramuscular administration in the vaccine kit is not particularly limited and may be appropriately selected depending on the number of times for use, and the content of a virus liquid containing the PEDV inactivated vaccine for intramuscular administration.

The vaccine kit may include the inactivated vaccine of PEDV for intramuscular administration and the adjuvant for intramuscular administration, as individual constituents or in a state of a composition obtained by mixing them.

As the composition obtained by mixing the inactivated vaccine of PEDV for intramuscular administration and the adjuvant for intramuscular administration, a vaccine of the present invention for intramuscular administration, which will be described hereinafter, is suitably used.

<Other Constituents>

The other constituents are not particularly limited and may be appropriately selected depending on the intended purpose, so long as the effects of the present invention are not compromised. Examples thereof include a dissolution liquid, physiological saline for dilution, a container for preparation in use, a syringe, an injection needle, and a package insert.

The formulation of the dissolution liquid is not particularly limited and may be appropriately selected depending on the intended purpose. Examples thereof include those described in the item of other ingredients in the vaccine of the present invention for oral or nasal administration, which will be described hereinafter.

<Method for Use>

The vaccine kit is used by administering the live vaccine of PEDV for oral or nasal administration and the adjuvant for oral or nasal administration through oral administration or nasal administration, and then administering the inactivated vaccine of PEDV for intramuscular administration and the adjuvant for intramuscular administration through intramuscular administration.

The live vaccine of PEDV for oral or nasal administration and the adjuvant for oral or nasal administration may be simultaneously administered or may be separately administered. However, simultaneous administration is preferable regarding simplicity.

When the live vaccine of PEDV for oral or nasal administration and the adjuvant for oral or nasal administration are simultaneously administered to a pig through oral administration or nasal administration, the composition obtained by mixing the live vaccine of PEDV for oral or nasal administration and the adjuvant for oral or nasal administration is preferably used.

When the live vaccine of PEDV for oral or nasal administration and the adjuvant for oral or nasal administration are separately administered to a pig through oral administration or nasal administration, the order of administration of the live vaccine of PEDV for oral or nasal administration and the adjuvant for oral or nasal administration is not particularly limited and may be appropriately selected depending on the intended purpose.

A dosage interval between the live vaccine of PEDV for oral or nasal administration and the adjuvant for oral or nasal administration is not particularly limited and may be appropriately selected depending on the intended purpose, so long as the adjuvant effects of the adjuvant for oral or nasal administration can be achieved.

The inactivated vaccine of PEDV for intramuscular administration and the adjuvant for intramuscular administration may be simultaneously administered or may be separately administered. However, simultaneous administration is preferable regarding simplicity.

When the inactivated vaccine of PEDV for intramuscular administration and the adjuvant for intramuscular administration are simultaneously administered to the pig through intramuscular administration, the composition obtained by mixing the inactivated vaccine of PEDV for intramuscular administration and the adjuvant for intramuscular administration is preferably used.

When the inactivated vaccine of PEDV for intramuscular administration and the adjuvant for intramuscular administration are separately administered to the pig through intramuscular administration, the order of administration of the inactivated vaccine of PEDV for intramuscular administration and the adjuvant for intramuscular administration is not particularly limited and may be appropriately selected depending on the intended purpose.

A dosage interval between the inactivated vaccine of PEDV for intramuscular administration and the adjuvant for intramuscular administration is not particularly limited and may be appropriately selected depending on the intended purpose, so long as the adjuvant effects of the adjuvant for intramuscular administration can be achieved.

The vaccine kit can be suitably used for the above-described method of the present invention for preventing or treating porcine epidemic diarrhea.

(Vaccine for Oral or Nasal Administration)

A vaccine of the present invention for oral or nasal administration includes a live vaccine of a porcine epidemic diarrhea virus and an adjuvant and further comprises other ingredients if necessary.

The vaccine for oral or nasal administration is used for a pig which is subsequently given booster immunization through intramuscular administration of an inactivated vaccine of the porcine epidemic diarrhea virus and an adjuvant.

<Live Vaccine of Porcine Epidemic Diarrhea Virus (PEDV)>

The classification and the acquisition method of the PEDV used for the live vaccine of PEDV, and a method for attenuating pathogenicity of the PEDV are not particularly limited and may be appropriately selected depending on the intended purpose. Examples thereof include aspects described in the item of the live vaccine of PEDV in the first administration step of the method of the present invention for preventing or treating porcine epidemic diarrhea as described above.

The content of the live vaccine of PEDV in the vaccine for oral or nasal administration is not particularly limited and may be appropriately selected depending on the intended purpose, but is preferably $10^{7.0}$ TCID$_{50}$/dose or more. When the content thereof is less than $10^{7.0}$ TCID$_{50}$/dose, production of the neutralizing antibody specific to the PEDV and induction of the humoral immune response cannot be achieved, and the porcine epidemic diarrhea cannot be prevented or treated in some cases.

<Adjuvant>

The kind of the adjuvant is not particularly limited and may be appropriately selected depending on the intended purpose. Examples thereof include those described in the item of the adjuvant in the first administration step of the method of the present invention for preventing or treating porcine epidemic diarrhea as described above.

Among them, microemulsion adjuvants, cholera toxins, E. coli heat-labile enterotoxins, CpG oligonucleotide, polyinosinic-polycytidylic acid (poly (I:C)), polymer adjuvants, and squalene are preferable, microemulsion adjuvants are more preferable.

An aspect of the microemulsion adjuvant is the same as described in the item of the adjuvant in the first administration step of the method of the present invention for preventing or treating porcine epidemic diarrhea as described above.

The content of the adjuvant in the vaccine for oral or nasal administration is not particularly limited and may be appropriately selected depending on the intended purpose, so long as the effects of the live vaccine of PEDV are not compromised and the adjuvant effects can be achieved.

When the adjuvant is the microemulsion adjuvant, the content of the microemulsion adjuvant in the vaccine for oral or nasal administration is not particularly limited and may be appropriately selected depending on the intended purpose. The content thereof is preferably 20% by volume to 80% by volume, particularly preferably 50% by volume. When the content of the microemulsion is less than 20% by volume, production of the neutralizing antibody specific to the PEDV and induction of the humoral immune response cannot be achieved, and the porcine epidemic diarrhea cannot be prevented or treated in some cases. When the content thereof is more than 80% by volume, swelling, induration, redness, pyrexia, and anaphylaxis shock will be caused on the administered portion, production of the neutralizing antibody specific to the PEDV and induction of the humoral immune response cannot be achieved, and the porcine epidemic diarrhea cannot be prevented or treated in some cases.

<Other Ingredients>

The other ingredients are not particularly limited and may be appropriately selected from pharmaceutically acceptable carriers depending on the intended purpose. Examples thereof include additive agents, pharmaceutic aids, and water. These may be used alone or in combination.

The additive agent or the pharmaceutic aid is not particularly limited and may be appropriately selected depending on the intended purpose. Examples thereof include bactericides, preservatives, binders, thickeners, fixing agents, bonding agents, colorants, stabilizers, pH adjusters, buffers, tonicity agents, solvents, antioxidants, ultraviolet inhibitors, crystallization inhibitors, antifoaming agents, property-improving agents, and antiseptics.

The bactericide is not particularly limited and may be appropriately selected depending on the intended purpose. Examples thereof include cationic surfactants such as benzalkonium chloride, benzethonium chloride, and cetylpyridinium chloride.

The preservative is not particularly limited and may be appropriately selected depending on the intended purpose. Examples thereof include para-hydroxybenzonate, chlorobutanol, cresol, thimerosal, and phenoxyethanol.

The binder, the thickener, or the fixing agent is not particularly limited and may be appropriately selected depending on the intended purpose. Examples thereof include starch, dextrin, cellulose, methyl cellulose, ethyl cellulose, carboxymethyl cellulose, hydroxyethyl cellulose, hydroxypropyl cellulose, hydroxypropyl methylcellulose, carboxymethyl starch, pullulan, sodium alginate, ammonium alginate, propylene glycol alginate, guar gum, locust bean gum, gum arabic, xanthan gum, gelatin, casein, polyvinyl alcohol, polyethylene oxide, polyethylene glycol, ethylene propylene block polymer, sodium polyacrylate, and polyvinyl pyrrolidone.

The bonding agent is not particularly limited and may be appropriately selected depending on the intended purpose. Examples thereof include water, ethanol, propanol, simple syrup, a glucose solution, a starch solution, a gelatin solution, carboxymethyl cellulose, hydroxypropyl cellulose, hydroxypropyl starch, methyl cellulose, ethyl cellulose, shellac, calcium phosphate, and polyvinyl pyrrolidone.

The colorant is not particularly limited and may be appropriately selected depending on the intended purpose. Examples thereof include titanium oxide and iron oxide.

The stabilizer is not particularly limited and may be appropriately selected depending on the intended purpose. Examples thereof include tragacanth, gum arabic, gelatin, sodium pyrosulfite, ethylenediaminetetraacetic acid (EDTA), thioglycolic acid, and thiolactic acid.

The pH adjuster or the buffer is not particularly limited and may be appropriately selected depending on the intended purpose. Examples thereof include sodium citrate, sodium acetate, and sodium phosphate.

The tonicity agent is not particularly limited and may be appropriately selected depending on the intended purpose. Examples thereof include sodium chloride, potassium chloride, and glucose.

The content of the other ingredients in the vaccine for oral or nasal administration is not particularly limited and may be appropriately selected depending on the intended purpose, so long as the effects of the present invention are not compromised.

<Dosage Form>

A dosage form of the vaccine for oral or nasal administration is not particularly limited and may be appropriately selected depending on the intended purpose, so long as oral administration or nasal administration can be performed. Examples thereof include solid formulation and liquid formulation. Among them, the vaccine for oral administration is preferably the solid formulation or the liquid formulation, and the vaccine for nasal administration is preferably liquid formulation.

—Solid Formulation—The solid formulation is not particularly limited and may be appropriately selected depending on the intended purpose. Examples thereof include hard capsules and soft capsules.

—Liquid Formulation—

The liquid formulation is not particularly limited and may be appropriately selected depending on the intended purpose. Examples of liquid formulation used as the vaccine for oral administration include syrups, health drinks, suspensions, spirits, and dietary agents.

Examples of the liquid formulation used as the vaccine for nasal administration include liquid formulations, eye drops, aerosol agents, and spray agents.

<Production Method>

A method for producing the vaccine for oral or nasal administration is not particularly limited and may be appropriately selected depending on the intended purpose from known methods according to the dosage form, so long as the live vaccine of PEDV and the adjuvant can be mixed.

<Use>

The vaccine for oral or nasal administration is used for a pig which is subsequently given booster immunization through intramuscular administration of the inactivated vaccine of PEDV and the adjuvant.

A method for giving booster immunization to the pig is not particularly limited and may be appropriately selected depending on the intended purpose. The method described in the second step of the method for preventing or treating the porcine epidemic diarrhea is suitably used.

The vaccine for oral or nasal administration may be used alone or may be used in combination with a medicine containing other ingredients as active ingredients. Moreover, the vaccine for oral or nasal administration may be used in such a state that the vaccine for oral or nasal administration is mixed with, for example, a medicine containing other ingredients as active ingredients, feed, or drinking water.

The vaccine for oral or nasal administration can induce production of the neutralizing antibody specific to the PEDV, by subsequently giving booster immunization through intramuscular administration of the inactivated vaccine of PEDV and the adjuvant, and further can induce production of IgA specific to the PEDV through the humoral immune response. As a result, it is possible to effectively prevent or treat porcine epidemic diarrhea.

The vaccine for oral or nasal administration can be directly administered not only to a sow but also to a piglet. Therefore, even when a piglet cannot take in the milk due to any reason or his sow has a low concentration of the neutralizing antibody against the PEDV in the milk, infection of the piglet with PEDV can be prevented or treated, which is advantageous.

(Vaccine for Intramuscular Administration)

A vaccine of the present invention for intramuscular administration includes an inactivated vaccine of the porcine epidemic diarrhea virus and an adjuvant and further comprises other ingredients if necessary.

The vaccine for intramuscular administration is used for a pig which has been given priming immunization through oral administration or nasal administration of a live vaccine of the porcine epidemic diarrhea virus and an adjuvant.

<Inactivated Vaccine of Porcine Epidemic Diarrhea Virus (PEDV)>

The classification and the acquisition method of the PEDV used for the inactivated vaccine of PEDV, and a method for inactivating infectivity of the PEDV are not particularly limited and may be appropriately selected depending on the intended purpose. Examples thereof include the aspects described in the item of the inactivated vaccine of PEDV in the second administration step of the method of the present invention for preventing or treating porcine epidemic diarrhea as described above.

The content of the inactivated vaccine of PEDV in the vaccine for intramuscular administration is not particularly limited and may be appropriately selected depending on the intended purpose. The content thereof is preferably $10^{6.5}$ $TCID_{50}$/dose or more, more preferably $10^{7.5}$ $TCID_{50}$/dose or more. When the content thereof is less than $10^{6.5}$ $TCID_{50}$/dose, production of the neutralizing antibody specific to the PEDV and induction of the humoral immune response cannot be achieved, and the porcine epidemic diarrhea cannot be prevented or treated in some cases.

<Adjuvant>

The kind of the adjuvant is not particularly limited and may be appropriately selected depending on the intended purpose. Examples thereof include those described in the item of the adjuvant in the first administration step of the method of the present invention for preventing or treating porcine epidemic diarrhea as describe above.

Among them, for example, aluminum salts, microemulsion adjuvants, polymer adjuvants, dextrin derivatives, liquid paraffin, squalene, tocopherol acetate, and polysorbate are preferable, microemulsion adjuvants are particularly preferred.

An aspect of the microemulsion adjuvant is the same as those described in the item of the adjuvant in the first administration step of the method of the present invention for preventing or treating porcine epidemic diarrhea as described above.

The content of the adjuvant in the vaccine for intramuscular administration is not particularly limited and may be appropriately selected depending on the intended purpose, so long as the effects of the inactivated vaccine of PEDV are not compromised and the adjuvant effects can be achieved.

When the adjuvant is the microemulsion adjuvant, the content of the microemulsion adjuvant in the vaccine for intramuscular administration is not particularly limited and may be appropriately selected depending on the intended purpose. The content thereof is preferably 20% by volume to 80% by volume, particularly preferably 50% by volume. When the content of the microemulsion is less than 20% by volume, production of the neutralizing antibody specific to the PEDV and induction of the humoral immune response cannot be achieved, and the porcine epidemic diarrhea cannot be prevented or treated in some cases. When the content thereof is more than 80% by volume, swelling, induration, redness, pyrexia, and anaphylaxis shock will be caused on the administered portion, production of the neutralizing antibody specific to the PEDV and induction of the humoral immune response cannot be achieved, and the porcine epidemic diarrhea cannot be prevented or treated in some cases.

<Other Ingredients>

The other ingredients are not particularly limited and may be appropriately selected from pharmaceutically acceptable carriers depending on the intended purpose. Examples thereof include those described in the item of the other ingredients of the vaccine for oral or nasal administration.

The content of the other ingredients in the vaccine for intramuscular administration is not particularly limited and may be appropriately selected depending on the intended purpose, so long as the effects of the present invention are not compromised.

<Dosage Form>

A dosage form of the vaccine for intramuscular administration is not particularly limited and may be appropriately selected depending on the intended purpose, so long as it is possible to perform intramuscular administration. Examples thereof include injection agents.

—Injection Agent—

The injection agent is not particularly limited and may be appropriately selected depending on the intended purpose. Examples thereof include solutions, suspensions, and solid formulations to be dissolved in use.

<Production Method>

A method for producing the vaccine for intramuscular administration is not particularly limited and may be appropriately selected depending on the intended purpose from known methods according to the dosage form, so long as the inactivated vaccine of PEDV and the adjuvant can be mixed.

<Use>

The vaccine for intramuscular administration is used for a pig which has been given priming immunization through oral administration or nasal administration of the live vaccine of PEDV and the adjuvant.

A method for giving priming immunization to the pig is not particularly limited and may be appropriately selected depending on the intended purpose. The method described in the first step of the method for preventing or treating porcine epidemic diarrhea is suitably used.

The vaccine for intramuscular administration may be used alone or may be used in combination with a medicine containing other ingredients as active ingredients. Moreover, the vaccine for intramuscular administration may be used in such a state that the vaccine for intramuscular administration is mixed with, for example, a medicine containing other ingredients as active ingredients.

When the vaccine for intramuscular administration is used for the pig which has been given priming immunization through oral administration or nasal administration of the live vaccine of PEDV and the adjuvant, it is possible to induce production of the neutralizing antibody specific to the PEDV and to further induce production of IgA specific to the PEDV through the humoral immune response. As a result, it is possible to prevent or treat porcine epidemic diarrhea effectively.

The vaccine for intramuscular administration can be directly administered not only to a sow but also to a piglet. Therefore, even when a piglet cannot take in the milk due to any reason or his sow has a low concentration of the neutralizing antibody against the PEDV in the milk, infection of the piglet with PEDV can be prevented or treated, which is advantageous.

EXAMPLES

The present invention will be described in detail by way of Examples. The present invention should not be construed as being limited to these Examples.

Production Example 1

<Production of PEDV (P-5V Strain) Live Vaccine 1>
<<Isolation and Preparation of P-5V Strain of PEDV>>

The small intestine was collected from a pig that had developed the porcine epidemic diarrhea (PED) in a field and was used to form a 10% by mass tissue homogenate. The 10% by mass tissue homogenate was orally administered to a piglet that had not been infected with the PED. After two days, the small intestine was collected and was used for preparing a 10% by mass tissue homogenate. The tissue homogenate obtained was subcultured in the piglet that had not been infected with the PED for three generations in the same manner as described above. To the tissue homogenate obtained from the piglet at a passage stage of the third generation, trypsin was added so as to be a final concentration of 10 µg/mL. Then, the resultant was inoculated into Vero cells that had been made confluent in a 25 $cm^2$-culture flask in advance and was cultured at 37° C. for 60 minutes. Then, 5 mL of a culture medium (hereinafter may be referred to as "10 µg/mL trypsin-added culture medium") prepared by the method described below was added thereto, and the resultant was cultured at 37° C. The cytopathic effect (CPE) was confirmed using an optical microscope every day. At a point of time when the CPE was confirmed, the culture was terminated. For the passage of the isolated virus, as the passage proceeded, the amount of trypsin added was gradually decreased. Finally, trypsin was not added thereto, and the passage culture was performed for 100 generations.

—10 µg/mL Trypsin-Added Culture Medium—

In 500 mL of Minimal Essential Media (MEM) (available from Thermo Fisher Scientific), a yeast extract (available from Difco Laboratories) and Tryptose Phosphate Broth (available from Difco Laboratories) were dissolved so that a final concentration of the yeast extract was 0.02% (w/v), and a final concentration of Tryptose Phosphate Broth was 0.03% (w/v). Then, penicillin (50,000 units), streptomycin (50 mg), and trypsin were dissolved therein so that a final concentration of the trypsin was 10 µg/mL.

<<Identification of P-5V Strain>>

TRIZol (Registered Trademark) reagent (available from Thermo Fisher Scientific) was used to extract the virus RNA from the culture supernatant of the P-5V strain. The PEDV RNA was amplified with a thermal cycler (Veriti 96-Well Thermal Cycler, available from Thermo Fisher Scientific) through the RT-PCR using SuperScript (Registered Trademark) III One-Step RT-PCR System (available from Thermo Fisher Scientific) and eight kinds of the primer sets specific to the PEDV S gene (primer sets 1 to 8) presented in the following Table 1. The amplified RT-PCR product was inserted into pCR (Registered Trademark) 2.1-TOPO TA vector (available from Thermo Fisher Scientific), and it was transformed into *E. coli* TOP10 (available from Thermo Fisher Scientific) through heat shock, followed by cloning. *E. coli* was cultured overnight at 37° C. using an LB broth (formulation: sodium chloride (10 g), Bacto Trypton (10 g), and a yeast extract (5 g) were dissolved in distilled water (1 L)). Then, QIAprep Spin Miniprep Kit (available from QIAGEN) was used to purify the plasmid. From the purified plasmid, the base sequence of the PEDV S gene was sequenced through BigDye (Registered Trademark) Terminator v3.1 reagent and 3130xl Genetic Analyzer (available from Applied Biosystems). Each sequence fragment that had been sequenced was assembled, and the phylogenetic analysis through the neighbor-joining method was performed using MEGA4.0 software.

As a result, the strain obtained above was identified as the P-5V strain of the genetic Group I of PEDV (see FIG. 1).

TABLE 1

| Primer set | Primer name | Sequence | SEQ ID NO: |
|---|---|---|---|
| 1 | 1-F | 5'-GTGGCTTTTCTAATCATTTGGTC-3' | 1 |
|   | 1-R | 5'-GCACTAGTAACATTAAGCATGTA-3' | 2 |
| 2 | 2-F | 5'-TTGTCGGCATAACATGGG-3' | 3 |
|   | 2-R | 5'-GTTGTAAGTATCCACTTTAAGAAA-3' | 4 |
| 3 | 3-F | 5'-AAGGCTCAATTGTACTTCAT-3' | 5 |
|   | 3-R | 5'-TCAACACAGAAAGAACTAAACC-3' | 6 |
| 4 | 4-F | 5'-CAGCCAATTTCTTTTGTTACT-3' | 7 |
|   | 4-R | 5'-TGCTCTGAAAAAGAACATGG-3' | 8 |
| 5 | 5-F | 5'-ACATCTGATTCTGGACAGTT-3' | 9 |
|   | 5-R | 5'-AGACCTTTTTGTACCACCCT-3' | 10 |
| 6 | 6-F | 5'-ATTTCTGAAGAGGCTCTACAGT-3' | 11 |
|   | 6-R | 5'-CTAGAAATGGCTTGGAAGTT-3' | 12 |
| 7 | 7-F | 5'-CTCATGCGCTTACTAAGGTT-3' | 13 |
|   | 7-R | 5'-CATCGATGTAATCTGGGATTA-3' | 14 |
| 8 | 8-F | 5'-CCTAGAAAACCTACCGTTAGTG-3' | 15 |
|   | 8-R | 5'-AGCTCCAACTCTTGGACAGC-3' | 16 |

<<Preparation of PEDV (P-5V strain) Concentrated Virus Antigen Liquid 1>

The P-5V strain was inoculated into Vero cells and was cultured at 37° C. for 3 days. The Vero cells were collected and then were subjected to freezing and thawing. Next, the product obtained through freezing and thawing was centrifuged, and the thus-obtained supernatant was collected as "PEDV (P-5V strain) virus antigen liquid 1". To the PEDV (P-5V strain) virus antigen liquid 1, 7.5% (w/v) polyethylene glycol 6000 and 1M sodium chloride were added. The resultant was stirred at 4° C. overnight and the precipitates were collected through centrifugal separation. The precipitates were dissolved in physiological saline in such an amount that is one-twentieth the amount (v/v) of the PEDV (P-5V strain) virus antigen liquid 1. Then, the resultant was centrifuged again, and the thus-obtained supernatant was collected as "PEDV (P-5V strain) concentrated virus antigen liquid 1".

—Measurement of Virus Titer—

The virus titer (virus infectivity titer) of the PEDV (P-5V strain) concentrated virus antigen liquid 1 was measured through the 50% Tissue Culture Infective Dose: $TCID_{50}$.

Specifically, Vero cells were seeded into a 24-well cell culture plate at $0.75 \times 10^6$ cell/0.5 ml/well and were cultured at 37° C. for 3 days. An antigen liquid to be measured (here, the PEDV (P-5V strain) concentrated virus antigen liquid 1) was subjected to the 10-fold serial dilution in a culture medium. Here, the culture medium was obtained as described below. Specifically, in MEM (500 mL) (available from Thermo Fisher Scientific), a yeast extract (available from Difco Laboratories) and Tryptose Phosphate Broth (available from Difco Laboratories) were dissolved so that a final concentration of the yeast extract was 0.02% (w/v) and a final concentration of Tryptose Phosphate Broth was 0.03% (w/v). Then, penicillin (50,000 units) and streptomycin (50 mg) were dissolved therein. The resultant was inoculated into Vero cells, and the cells were cultured at 37° C. for 90 minutes. After the culture medium was changed, the culture was performed at 37° C. for 7 days. The cytopathic effect (CPE) was observed using an optical microscope and the virus titer ($TCID_{50}$) was calculated according to the Reed-Muench.

As a result, the virus titer of the PEDV (P-5V strain) concentrated virus antigen liquid 1 was $10^{7.75}$ $TCID_{50}$/mL.

<<Preparation of PEDV (P-5V Strain) Live Vaccine 1>>

The PEDV (P-5V strain) concentrated virus antigen liquid 1 and microemulsion (product name: MONTANIDE IMS1313 VG, available from SEPPIC) were mixed in equal amounts (v/v) and were stirred at room temperature (25±5° C.) for 5 minutes or more, to form "PEDV (P-5V strain) live vaccine 1".

Production Example 2

<Production of PEDV (P-5V Strain) Live Vaccine 2>
<<Preparation of PEDV (P-5V Strain) Concentrated Virus Antigen Liquid 2>>

The P-5V strain of PEDV that had been isolated and prepared in Production Example 1 was inoculated into Vero cells and was cultured at 37° C. for 3 days. The Vero cells were collected and then were subjected to freezing and thawing. Next, the product obtained through freezing and thawing was centrifuged, and the thus-obtained supernatant was collected as "PEDV (P-5V strain) virus antigen liquid 2". To the PEDV (P-5V strain) virus antigen liquid 2, 7.5% (w/v) polyethylene glycol 6000 and 1M sodium chloride were each added. The resultant was stirred at 4° C. overnight, and the precipitates were collected through centrifugal separation. The precipitates were dissolved in physiological saline in such an amount that is one-twentieth the amount (v/v) of the PEDV (P-5V strain) virus antigen liquid 2. Then, the resultant was centrifuged again, and the thus-obtained supernatant was collected as "PEDV (P-5V strain) concentrated virus antigen liquid 2".

The virus titer of the PEDV (P-5V strain) concentrated virus antigen liquid 2 was measured through the $TCID_{50}$ method described in the item of the "Measurement of virus titer" in the Production Example 1. As a result, the virus titer of the PEDV (P-5V strain) concentrated virus antigen liquid 2 was $10^{7.75}$ $TCID_{50}$/mL.

<<Preparation of PEDV (P-5V Strain) Live Vaccine 2>>

The PEDV (P-5V strain) concentrated virus antigen liquid 2 and the microemulsion prepared in Production Example 1 were mixed in equal amounts (v/v) and were stirred at room temperature (25±5° C.) for 5 minutes or more, to form "PEDV (P-5V strain) live vaccine 2".

Production Example 3

<Production of PEDV (P-5V Strain) Inactivated Vaccine 1>
<<Preparation of PEDV (P-5V Strain) Inactivated Virus Antigen Liquid 1>>

To the PEDV (P-5V strain) concentrated virus antigen liquid 1 obtained in the Production Example 1, neutral buffer formalin (available from KANTO CHEMICAL CO., INC.) was added so as to have a final concentration of 0.2% (v/v). The resultant was stirred at 4° C. for 48 hours to inactivate the PEDV (P-5V strain) virus antigen, obtaining "PEDV (P-5V strain) inactivated vaccine 1".

<<Preparation of PEDV (P-5V Strain) Inactivated Vaccine 1>>

The PEDV (P-5V strain) inactivated virus antigen liquid 1 and the microemulsion prepared in Production Example 1 were mixed in equal amounts (v/v) and were stirred at room temperature (25±5° C.) for 5 minutes or more, to form "PEDV (P-5V strain) inactivated vaccine 1".

Production Example 4

<Production of PEDV (P-5V Strain) Inactivated Vaccine 2>
<<Preparation of PEDV (P-5V Strain) Inactivated Virus Antigen Liquid 2>>

To the PEDV (P-5V strain) concentrated virus antigen liquid 2 obtained in the Production Example 2, neutral buffer formalin (available from KANTO CHEMICAL CO., INC.) was added so as to have a final concentration of 0.2% (v/v). The resultant was stirred at 4° C. for 48 hours to inactivate the PEDV (P-5V strain) virus antigen, obtaining "PEDV (P-5V strain) inactivated virus antigen liquid 2".

<<Preparation of PEDV (P-5V Strain) Inactivated Vaccine 2>>

The PEDV (P-5V strain) inactivated virus antigen liquid 2 and the microemulsion prepared in Production Example 1 were mixed in equal amounts (v/v) and were stirred at room temperature (25±5° C.) for 5 minutes or more, to form "PEDV (P-5V strain) inactivated vaccine 2".

Example 1

<Priming Immunization>

To an eight-week-old pig negative for the PED antibody, the PEDV (P-5V strain) live vaccine 1 (10 mL, $10^{8.0}$ $TCID_{50}$/dose) produced in Production Example 1 was orally administered once.

<Booster Immunization>

Four weeks after the priming immunization, the PEDV (P-5V strain) inactivated vaccine 1 (2 mL, $10^{7.5}$ $TCID_{50}$/dose) produced in Production Example 3 was intramuscularly administered (injected) once.

Comparative Example 1

<Priming Immunization>

To an eight-week-old pig negative for the PED antibody, the PEDV (P-5V strain) concentrated virus antigen liquid (10 mL, $10^{8.0}$ $TCID_{50}$/dose) produced in Production Example 1 was orally administered once.

<Booster Immunization>

Four weeks after the priming immunization, the PEDV (P-5V strain) inactivated vaccine 1 (2 mL, $10^{7.5}$ $TCID_{50}$/dose) produced in Production Example 3 was intramuscularly administered (injected) once.

Comparative Example 2

<Priming Immunization>

To an eight-week-old pig negative for the PED antibody, NISSEIKEN PED live vaccine (available from Nisseiken Co., Ltd) (2 mL) was intramuscularly administered (injected) once.

<Booster Immunization>

Four weeks after the priming immunization, NISSEIKEN PED live vaccine (available from Nisseiken Co., Ltd) (2 mL) was intramuscularly administered (injected) once.

TABLE 2

| | Priming immunization | | Booster immunization | | |
|---|---|---|---|---|---|
| | Vaccine | Administration method | Vaccine | Administration method | Immunization interval |
| Example 1 | PEDV (P-5V strain) live vaccine 1 | Oral administration | PEDV (P-5V strain) inactivated vaccine 1 | Intramuscular administration | 4 weeks |
| Comparative Example 1 | PEDV (P-5V strain) concentrated virus antigen liquid | Oral administration | PEDV (P-5V strain) inactivated vaccine 1 | Intramuscular administration | 4 weeks |
| Comparative Example 2 | NISSEIKEN PED live vaccine | Intramuscular administration | NISSEIKEN PED live vaccine | Intramuscular administration | 4 weeks |

Test Example 1

The blood was collected from the pigs of Example 1, Comparative Example 1, and Comparative Example 2, immediately before the priming immunization and one week after the booster immunization. Moreover, as a control, the blood was collected from an eight-week-old pig that was negative for the PED antibody and had undergone neither the priming immunization nor the booster immunization, when the pig was 8 weeks old, 12 weeks old, and 13 weeks old. Next, the PEDV neutralizing antibody titer in the collected blood was measured, and the production induction of IgA against the PEDV was examined in the following manners.

<Measurement of PEDV Neutralizing Antibody Titer>

Vero cells were seeded into a 24-well cell culture plate at $0.75\times10^{6}$ cell/0.5 ml/well and were cultured at 37° C. for 3 days. The pig serum obtained through the 2-fold serial dilution with a culture medium was mixed with a virus liquid containing the P-5V strain (200 $TCID_{50}$) in equal amounts, and the resultant was allowed to react at 37° C. for 90 minutes. Here, the culture medium was obtained as described below. Specifically, in MEM (500 mL) (available from Thermo Fisher Scientific), a yeast extract (available from Difco Laboratories) and Tryptose Phosphate Broth (available from Difco Laboratories) were dissolved so that a final concentration of the yeast extract was 0.02% (w/v), and a final concentration of Tryptose Phosphate Broth was 0.03% (w/v). Then, penicillin (50,000 units) and streptomycin (50 mg) were dissolved therein. The mixture liquid of the serum and the P-5V strain was inoculated into the Vero cells and was cultured at 37° C. for 90 minutes. After the culture medium was changed, the culture was performed at 37° C. for 7 days. The cytopathic effect (CPE) was observed using an optical microscope and the PEDV neutralizing antibody titer was measured. Results are presented in the following Table 3. Note that, the unit of the neutralizing antibody titer is presented by a dilution rate (fold) of the serum.

<Production Induction of IgA Against PEDV>

<<Detection of IgA against PEDV Through Western Blotting>>

In Example 1, Comparative Example 1, and Comparative Example 2, each blood collected one week after the booster immunization was centrifuged to separate the serum. Then, 200 μl of the virus liquid containing the P-5V strain ($10^{7.0}$ TCID$_{50}$/mL) was electrophoresed on the SDS-PAGE gel, the following blotting onto a polyvinylidene difluoride (PVDF) filter (available from Merck Millipore). The pig serum, which was 100-fold diluted in PBS (formulation: NaCl 8 g, KCl 0.2 g, Na$_2$HPO$_4$/12H$_2$O 2.9 g, and KH$_2$PO$_4$ 0.2 g dissolved in distilled water (1 L). The same formulation is applied to the following Test Examples) to which 3% (w/v) skim milk and 0.05% (w/v) Tween20 were added, as a primary antibody, and an HRP-labeled, anti-pig IgA polyclonal antibody (available from Acris Antibodies) as a secondary antibody were used to detect the IgA against the PEDV by using a detection reagent (product name: ECL Prime Western Blotting Detection Reagent, available from GE Healthcare).

From the results of the Western blotting, presence or absence of the production induction of IgA against the PEDV was evaluated based on the following evaluation criteria. Results are presented in the following Table 3.
—Evaluation Criteria—
"−": There was no production induction activity of IgA against the PEDV (No band was detected through Western blotting).
"+": There was production induction activity of IgA against the PEDV (The band was detected through Western blotting).

TABLE 3

| | PEDV neutralizing antibody titer (fold) | | Production induction of IgA against PEDV One week after booster immunization |
|---|---|---|---|
| | Immediately before priming immunization | One week after booster immunization | |
| Example 1 | <2 | 1,024 | + |
| Comparative Example 1 | <2 | 8 | − |
| Comparative Example 2 | <2 | 16 | − |
| Control | <2 | <2 | No test |

When the PEDV (P-5V strain) live vaccine containing the adjuvant was orally administered in the priming immunization (Example 1), significantly enhanced production activity of the neutralizing antibody specific to the PEDV and production induction activity of IgA specific to the PEDV were found, compared to the case where the PEDV containing no adjuvant (Comparative Example 1) and the case where the conventional vaccine for intramuscular administration was administered twice (Comparative Example 2).

Test Example 2

Two weeks after the booster immunization, the pigs of Example 1 and Comparative Example 1 were challenged, through oral administration, with MZ0116-2/2013 strain that was a field strain (hereinafter may be referred to as "field strain MZ") ($10^{5.0}$ TCID$_{50}$/mL) (5 mL) isolated and prepared in the following manners. As a control, a 14-week-old pig that was negative for the PED antibody and had undergone neither the priming immunization nor the booster immunization was challenged by orally administering the field strain MZ ($10^{5.0}$ TCID$_{50}$/mL) (5 mL) as described above. Then, the clinical symptoms thereof were observed, the PEDV RNAs in feces were detected, and the PEDV RNAs in the organs were detected in the following manners.

<<Isolation and Preparation of PEDV (MZ0116-2/2013 Strain (Field Strain MZ))>>

The small intestine was collected from the piglet which died of the porcine epidemic diarrhea (PED). Then, the small intestine (0.5 g) was charged into a beads disrupter tube (available from Bertin Technologies) and was crushed with a high-speed cell-disrupting machine (available from Precellys, Bertin Technologies). The resultant was suspended in a culture medium (MEM, available from Thermo Fisher Scientific) (5 mL), followed by centrifugal separation. The supernatant after the centrifugal separation was passed through a syringe filter (available from GE Healthcare Japan) having a pore size (pore diameter) of 0.22 μm to form a 10% by mass tissue emulsion thereby. Then, a mixture liquid obtained by mixing the 10% by mass tissue emulsion (300 μL) and a 10 μg/mL trypsin-added culture medium (100 μL) was prepared. The total amount of the mixture liquid was inoculated into Vero cells that had been made confluent in a 6-well cell culture plate in advance and was cultured at 37° C. for 90 minutes. Then, the mixture liquid was removed and a 10 μg/mL-trypsin-added culture medium (4 mL) was added to it, followed by the culture at 37° C. The cytopathic effect (CPE) was observed every day using an optical microscope, and the culture was terminated at a point of time the CPE was confirmed. The supernatant and the cells were collected and were subjected to freezing and thawing. Then, the centrifuged supernatant was passaged to the next subculture.

<<Identification of MZ0116-2/2013 Strain>>

The phylogenetic analysis was performed in the same manner as in the "Identification of P-5V strain" except that the culture supernatant of the P-5V strain was changed to the culture supernatant of the field strain MZ in the "Identification of P-5V strain" of Production Example 1.

As a result, the strain obtained above was identified as the field strain MZ of the genetic Group II of the PEDV (see FIG. 1).

<Observation of Clinical Symptoms>

The piglets of Example 1, Comparative Example 1, and the control were observed every day for the state of feces and appetite on Day 0 to Day 14 after challenge with the field strain MZ and were evaluated based on the following evaluation criteria. Results of the state of feces are presented in the following Table 4 and results of appetite are presented in the following Table 5.
—Evaluation Criteria of State of Feces—
"0": Normal feces
"1": Loose feces
"2": Diarrhea feces
"3": Watery diarrhea feces
—Evaluation Criteria of Appetite—
"0": Normal
"1": Mild anorexia
"2": Moderate anorexia
"3": Severe anorexia

TABLE 4

| State of feces | Day after challenge | | | | | | | | | | | | | | | |
|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | Total |
| Example 1 | 0 | 0 | 0 | 0 | 0 | 0 | 0 | 0 | 0 | 0 | 0 | 0 | 0 | 0 | 0 | 0 |
| Comparative Example 1 | 0 | 0 | 0 | 0 | 0 | 0 | 0 | 0 | 0 | 0 | 0 | 0 | 0 | 0 | 0 | 0 |
| Control | 0 | 0 | 0 | 0 | 0 | 0 | 0 | 0 | 0 | 0 | 0 | 0 | 0 | 0 | 0 | 0 |

TABLE 5

| Appetite | Day after challenge | | | | | | | | | | | | | | | |
|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | Total |
| Example 1 | 0 | 0 | 0 | 0 | 0 | 0 | 0 | 0 | 0 | 0 | 0 | 0 | 0 | 0 | 0 | 0 |
| Comparative Example 1 | 0 | 0 | 1 | 1 | 1 | 1 | 1 | 0 | 0 | 0 | 0 | 0 | 0 | 0 | 0 | 5 |
| Control | 0 | 0 | 0 | 2 | 2 | 1 | 1 | 0 | 0 | 0 | 0 | 0 | 0 | 0 | 0 | 6 |

The states of feces of Example 1, Comparative Example 1, and the control were zero points, and no difference was found (Table 4). Meanwhile, the appetite of Example 1 was found to exhibit "normal," but Comparative Example 1 and the control were found to exhibit anorexia (Table 5).

<Detection of PEDV RNA in Rectal Swab>

On Day 0 to Day 14 after the challenge with the field strain MZ in Example 1, Comparative Example 1, and the control, a sterilized cotton swab (available from Osaki Medical Corporation) was used to collect the rectal swab every day and was suspended in PBS (1 mL). The suspension was centrifuged and the virus mRNA was extracted with TRIZol (Registered Trademark) reagent (available from Thermo Fisher Scientific). The PEDV RNA was amplified with a thermal cycler (Veriti 96-Well Thermal Cycler, available from Thermo Fisher Scientific) through the RT-PCR using SuperScript (Registered Trademark) III One-Step RT-PCR System (available from Thermo Fisher Scientific) and primers specific to the PEDV (the primer 9-F [5'-GATATGTTTGTAATGGTAACTC-3'] set forth in SEQ ID NO: 17 and the primer 9-R [5'-AGCATAGCTAAAAGGCAATGC-3'] set forth in SEQ ID NO: 18). The amplified RT-PCR products were separated through the agarose gel electrophoresis, and the gel was dyed using ethidium bromide. Then, the PEDV RNA was detected through irradiation of ultraviolet rays. An incidence rate (%) of positive individuals from which the PEDV RNA was detected with respect to the population parameter in each group was calculated. Results thereof are presented in the following Table 6.

Comparative Example 1, and the control were extirpated and were used to prepare a 10% by mass tissue emulsion. The PEDV RNA in each organ was extracted from each 10% by mass tissue emulsion using TRIZol (Registered Trademark) reagent (available from Thermo Fisher Scientific). Then, the RNA amount (corresponding to $\log_{10}$ $TCID_{50}$/mL) was quantified through the real-time RT-PCR using GoTaq (Registered Trademark) 1-Step RT-qPCR System (available from Promega) and primers specific to the PEDV (the primer 10-F [5'-CGCAAAGACTGAACCCACTAAC-3'] set forth in SEQ ID NO: 19 and the primer 10-R [5'-TTGCCTCTGTTGTTACTTGGAGAT-3'] set forth in SEQ ID NO: 20) in StepOnePlus Real-Time PCR System (available from Thermo Fisher Scientific). Results are presented in the following Table 7.

TABLE 7

| | Spleen | Jejunum/ileum | Cecum | Colon | Mesenteric lymph node |
|---|---|---|---|---|---|
| Example 1 | ND | ND | ND | ND | ND |
| Comparative Example 1 | ND | 1.29E+02 | ND | ND | 5.05E+00 |
| Control | 5.78E+00 | 4.44E+01 | ND | ND | 1.10E+02 |

* ND: Below the detection limit

From the results of Table 6, the incidence rate of positive individuals from which the PEDV RNA was detected was high in Comparative Example 1 and the control. Meanwhile, positive individuals from which the PEDV RNA was

TABLE 6

| | Days after challenge | | | | | | | | | | | | | | |
|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 |
| Example 1 | 0 | 0 | 0 | 0 | 0 | 0 | 0 | 0 | 0 | 0 | 0 | 0 | 0 | 0 | 0 |
| Comparative Example 1 | 0 | 0 | 100 | 100 | 100 | 50 | 100 | 100 | 100 | 100 | 50 | 0 | 0 | 50 | 100 |
| Control | 0 | 0 | 0 | 100 | 100 | 100 | 100 | 100 | 100 | 100 | 0 | 0 | 50 | 75 | 25 |

Unit (%)

<Detection of PEDV RNA in Organs>

On Day 14 after challenge with the field strain MZ, the pancreas, the jejunum/ileum, the cecum, the colon, and the mesenteric lymph node of each individual of Example 1, detected did not appear in Example 1 during a period of observation. In addition, as seen from the results of Table 7, no PEDV RNA was also detected in each organ in Example 1.

It is believed that the secretory IgA secreted from the intestinal mucosa neutralizes the PEDV to achieve the protective immunity of infection in Example 1.

Here, as seen from Comparative Example 1 and the control in Table 6, it is known that even when the PEDVs are not detected once, the PEDVs appear again and continue to live for about 1 to 2 months after the infection.

Example 2

<Priming Immunization>

To an eight-week-old pig negative for the PED antibody, the PEDV (P-5V strain) live vaccine 2 (1 mL, $10^{7.45}$TCID$_{50}$/dose) produced in Production Example 2 was nasally administered once.

<Booster Immunization>

Six weeks after the priming immunization, the PEDV (P-5V strain) inactivated vaccine 2 (2 mL, $10^{7.75}$TCID$_{50}$/dose) produced in Production Example 4 was intramuscularly administered (injected) once.

Even when the PEDV (P-5V strain) live vaccine was nasally administered in the priming immunization, significantly enhanced production activity of the neutralizing antibody specific to the PEDV and production induction activity of IgA specific to the PEDV were found similarly to the case where it was orally administered.

Conventionally, there has been no report that the PEDV infects respiratory organs, and the infection with the PEDV is restricted to the digestive organs. Therefore, the fact that the nasal administration can induce production of the neutralizing antibody specific to the PEDV and the IgA specific to the PEDV is an unexpected finding by the present inventors.

TABLE 8

| | Priming immunization | | Booster immunization | | |
|---|---|---|---|---|---|
| | Vaccine | Administration method | Vaccine | Administration method | Immunization interval |
| Example 2 | PEDV (P-5V strain) live vaccine 2 | Nasal administration | PEDV (P-5V strain) inactivated vaccine 2 | Intramuscular administration | 6 weeks |

Test Example 3

The blood of the pig of Example 2 was collected immediately before the priming immunization and one week after the booster immunization. In addition, when an eight-week-old pig that was negative for the PED antibody and had undergone neither the priming immunization nor the booster immunization was 8 weeks old and 15 weeks old, the blood thereof was collected as a control. Next, the PEDV neutralizing antibody titer in the collected blood and production induction of IgA against the PEDV were examined in the same manners as in the method described in the <Measurement of PEDV neutralizing antibody titer> and the "Production induction of IgA against PEDV" in Test Example 1. Results are presented in the following Table 9.

TABLE 9

| | PEDV neutralizing antibody titer (fold) | | Production induction of IgA against PEDV |
|---|---|---|---|
| | Immediately before priming immunization | One week after booster immunization | One week after booster immunization |
| Example 2 | <2 | 2,048 | + |
| Control | <2 | <2 | − |

Test Example 4

Two weeks after the booster immunization, the pig of Example 2 was challenged with the field strain MZ ($10^{5.0}$ TCID$_{50}$/mL) (5 mL) through oral administration. As a control, a 16-week-old pig that was negative for the PED antibody and had undergone neither the priming immunization nor the booster immunization was challenged by orally administering the field strain MZ ($10^{5.0}$ TCID$_{50}$/mL) (5 mL) as described above. Then, detection of the PEDV RNA in the rectal swab and detection of the PEDV RNAs in the organs were performed in the same manners as described in the <Detection of PEDV RNA in rectal swab> of Test Example 2.

<Detection of PEDV RNA in Rectal Swab>

The incidence rate (%) of positive individuals from which the PEDV RNA was detected with respect to the population parameter in each group was calculated. Results are presented in the following Table 10.

TABLE 10

| | Days after challenge | | | | | | | | | | | | | | |
|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 |
| Example 2 | 0 | 0 | 0 | 0 | 33.3 | 0 | 0 | 33.3 | 33.3 | 0 | 0 | 0 | 0 | 0 | 33.3 |
| Control | 0 | 0 | 0 | 0 | 66.7 | 66.7 | 66.7 | 100 | 100 | 66.7 | 100 | 100 | 33.3 | 33.3 | 33.3 |

Unit (%)

<Detection of PEDV RNA in Organs>

On Day 14 after challenge with the field strain MZ, the jejunum/ileum, the cecum, the colon, and the mesenteric lymph node of each individual of Example 2 and the control were extirpated. The PEDV RNA in each organ was detected in the same manner as described in the <Detection of PEDV RNA in organs> of Test Example 2 to quantify the RNA amount (corresponding to $\log_{10}$ $TCID_{50}$/mL). Results are presented in the following Table 11.

TABLE 11

|  | Jejunum/ileum | Cecum | Colon | Mesenteric lymph node |
|---|---|---|---|---|
| Example 2 | ND | ND | ND | ND |
| Control | 1.64E+03 | ND | 1.23E+04 | 3.90E+03 |

* ND: Below the detection limit

Example 3

<Priming Immunization>

To a pregnant pig negative for the PED antibody, the PEDV (P-5V strain) live vaccine 2 (1 mL, $10^{7.45}TCID_{50}$/dose) produced in Production Example 2 was nasally administered once.

<Booster Immunization>

Eight weeks after the priming immunization, the PEDV (P-5V strain) inactivated vaccine 2 (2 mL, $10^{7.75}TCID_{50}$/dose) produced in Production Example 4 was intramuscularly administered (injected) once.

Comparative Example 3

<Priming Immunization>

To a pregnant pig negative for the PED antibody, NISSEIKEN PED live vaccine (available from Nisseiken Co., Ltd) (2 mL) was intramuscularly administered (injected) once.

<Booster Immunization>

Four weeks after the priming immunization, NISSEIKEN PED live vaccine (available from Nisseiken Co., Ltd) (2 mL) was intramuscularly administered (injected) once.

TABLE 12

|  | Priming immunization | | Booster immunization | | |
|---|---|---|---|---|---|
|  | Vaccine | Administration method | Vaccine | Administration method | Immunization interval |
| Example 3 | PEDV (P-5V strain) live vaccine 2 | Nasal administration | PEDV (P-5V strain) inactivated vaccine 2 | Intramuscular administration | 8 weeks |
| Comparative Example 3 | NISSEIKEN PED live vaccine | Intramuscular administration | NISSEIKEN PED live vaccine | Intramuscular administration | 4 weeks |

Test Example 5

Piglets (Day 2 after birth) borne from the pregnant pigs of Examples 3 and Comparative Example 3 were each challenged with the field strain MZ ($10^{5.0}$ $TCID_{50}$/mL) (5 mL) through oral administration. As a control, a piglet (Day 2 after birth) borne from the pregnant pig, which was negative for the PED antibody and had undergone neither the priming immunization nor the booster immunization, was challenged with the field strain MZ ($10^{5.0}$ $TCID_{50}$/mL) (5 mL) through oral administration. Here, after the piglets were challenged, the sows of Example 3 and Comparative Example 3 lived together with these piglets.

<PEDV Neutralizing Antibody Titer In Sow>

The blood of each of the pregnant pigs (sows) of Example 3, Comparative Example 3, and the control was collected immediately before the priming administration, one week after the boost administration, and one week after the piglet's challenge. The PEDV neutralizing antibody titer in the collected blood was examined in the same manner as in the method described in the <Measurement of PEDV neutralizing antibody titer> in Test Example 1. Results are presented in the following Table 13.

<Production Induction of IgA Against PEDV in the Milk of Sow>

Immediately before the piglets were challenged, the milk of each of the sows of Example 3, Comparative Example 3, and the control was collected. The IgA against the PEDV in the milk was detected in the same manner as in Test Example 1 except that the blood was changed to the milk in the method described in the <<Detection of IgA against PEDV through Western blotting>> of Test Example 1. Then, presence or absence of the production induction of IgA against the PEDV was evaluated in the same manner as in Test Example 1. Results are presented in the following Table 13.

TABLE 13

|  | PEDV neutralizing antibody titer (fold) | | | Production induction of IgA against PEDV in milk Immediately before piglet was challenged |
|---|---|---|---|---|
|  | Immediately before priming immunization | One week after booster immunization | One week after piglet was challenged |  |
| Example 3 | <2 | 1,024 | 1,024 | + |
| Comparative Example 3 | <2 | ND | 256 | − |
| Control | <2 | <2 | <2 | − |

<Survival Rate of Piglets>

On Day 0 to Day 7 after the piglets borne from the pregnant pigs of Example 3, Comparative Example 3, and the control were challenged with the field strain MZ, the survival rate thereof was confirmed every day. Results are presented in the following Table 14.

TABLE 14

| | Days after challenge | | | | | | | |
|---|---|---|---|---|---|---|---|---|
| | 0 | 1 | 2 | 3 | 4 | 5 | 6 | 7 |
| Example 3 | 100 | 100 | 100 | 100 | 87.5 | 87.5 | 87.5 | 87.5 |
| Comparative Example 3 | 100 | 100 | 87.5 | 75.0 | 75.0 | 75.0 | 75.0 | 75.0 |
| Control | 100 | 100 | 91.7 | 72.7 | 45.5 | 0 | 0 | 0 |

Unit: %

<Histopathological Observation of Small Intestine of Piglet>

The small intestine of each piglet extirpated in the <Detection of PEDV RNA in organs of piglets> was fixed with formalin and was used to prepare a paraffin section through the routine method. Next, xylene was used to remove paraffin from the paraffin section. Then, to re-hydrate the section, the section was immersed in aqueous ethanol solutions having concentration gradients to re-hydrate the section. After that, distilled water was used to remove ethanol. The section specimen from which ethanol had been removed was immersed in a hematoxylin solution for 20 minutes and was washed with distilled water. Then, the section specimen was immersed in an eosin solution for 2 minutes to be dyed. The section specimen was dehydrated by immersing it in aqueous ethanol solutions having concentration gradients and was immersed in xylene for clearing, to obtain a tissue specimen thereby. The tissue specimen prepared was observed using an optical microscope, and comprehensive evaluations such as atrophy of the villi, vacuolation of the villus cells, planarization of the villi, and inflammation of the villus basement membrane were performed based on the following evaluation criteria. Note that, several piglets were borne from one sow. Therefore, for scores of the evaluation criteria, an average value of scores of the piglets in each of the groups: Example 3, Comparative Example 3, and the control was calculated. Then, a significant difference was confirmed through the Student's t-test. Results are presented in the following Table 15.

—Evaluation Criteria—
 "0": Normal
 "1": Mild
 "2": Moderate
 "3": Severe

TABLE 15

| | Jejunum | Ileum |
|---|---|---|
| Example 3 | 1.27 ± 1.01[a,b] | 1.36 ± 1.12 |
| Comparative Example 3 | 2.00 ± 0.00[a] | 2.00 ± 0.58 |
| Control | 2.42 ± 0.67[b] | 2.08 ± 0.67 |

[a]There is a significant difference (p < 0.05, Student s t-test)
[b]There is a significant difference (p < 0.01, Student's t-test)

Aspects of the present invention are, for example, the following aspects.

<1> A method for preventing or treating porcine epidemic diarrhea, the method including:
 administering a live vaccine of a porcine epidemic diarrhea virus and an adjuvant to a pig through oral administration or nasal administration; and
 administering an inactivated vaccine of the porcine epidemic diarrhea virus and an adjuvant to the pig through intramuscular administration.

<2> The method for preventing or treating porcine epidemic diarrhea according to <1>,
 wherein the adjuvant is a microemulsion adjuvant.

<3> A vaccine kit including:
 a live vaccine of a porcine epidemic diarrhea virus for oral or nasal administration;
 an adjuvant for oral or nasal administration;
 an inactivated vaccine of the porcine epidemic diarrhea virus for intramuscular administration; and
 an adjuvant for intramuscular administration.

<4> The vaccine kit according to <3>,
 wherein the adjuvant for oral or nasal administration and the adjuvant for intramuscular administration are a microemulsion adjuvant.

<5> A vaccine for oral or nasal administration, the vaccine including:
 a live vaccine of a porcine epidemic diarrhea virus; and
 an adjuvant,
 wherein the vaccine is used for a pig which is subsequently given booster immunization through intramuscular administration of an inactivated vaccine of the porcine epidemic diarrhea virus and an adjuvant.

<6> The vaccine for oral or nasal administration according to <5>,
 wherein the adjuvant is a microemulsion adjuvant.

<7> A vaccine for intramuscular administration, the vaccine including:
 an inactivated vaccine of a porcine epidemic diarrhea virus; and
 an adjuvant,
 wherein the vaccine is used for a pig which has been given priming immunization through oral administration or nasal administration of a live vaccine of the porcine epidemic diarrhea virus and an adjuvant.

<8> The vaccine for intramuscular administration according to <7>,
 wherein the adjuvant is a microemulsion adjuvant.

INDUSTRIAL APPLICABILITY

In the present invention, the method for preventing or treating porcine epidemic diarrhea, the vaccine kit, the vaccine for oral or nasal administration, and the vaccine for intramuscular administration are excellent in the production induction activity of the neutralizing antibody specific to the porcine epidemic diarrhea virus and induction activity of the humoral immune response, and can be suitably used for preventing or treating the porcine epidemic diarrhea.

The invention claimed is:

1. A method for preventing porcine epidemic diarrhea, the method comprising the steps of:
   (a) administering a live, attenuated vaccine of a porcine epidemic diarrhea virus P-5V strain and a microemulsion adjuvant containing particles of 5 nm to 500 nm to a pig in need thereof through oral administration or nasal administration, wherein the live, attenuated vaccine is attenuated by culturing the porcine epidemic diarrhea virus P-5V strain for at least 100 passages in Vero cells; and
   (b) administering an inactivated vaccine of the porcine epidemic diarrhea virus P-5V strain and a microemulsion adjuvant containing particles of 5 nm to 500 nm to the pig through intramuscular administration, wherein the inactivated vaccine is inactivated by treating the live, attenuated vaccine with formalin, and
   wherein step (b) is carried out 1 week to 20 weeks after step (a).

2. The method for preventing porcine epidemic diarrhea according to claim 1, wherein a dose of the live, attenuated vaccine per one administration in the step (a) is $10^{7.0}$ $TCID_{50}$ or more and a dose of the inactivated vaccine per one administration in the step (b) is $10^{6.5}$ $TCID_{50}$ or more.

3. The method for preventing porcine epidemic diarrhea according to claim 1, wherein an antibody test to the porcine epidemic diarrhea virus in a serum of the pig in the step (a) is negative.

* * * * *

SEQUENCE LISTING

<160> NUMBER OF SEQ ID NOS: 20

<210> SEQ ID NO 1
<211> LENGTH: 23
<212> TYPE: DNA
<213> ORGANISM: artificial sequence

```
<220> FEATURE:
<223> OTHER INFORMATION: 1-F primer

<400> SEQUENCE: 1
gtggcttttc taatcatttg gtc                                          23

<210> SEQ ID NO 2
<211> LENGTH: 23
<212> TYPE: DNA
<213> ORGANISM: artificial sequence
<220> FEATURE:
<223> OTHER INFORMATION: 1-R primer

<400> SEQUENCE: 2
gcactagtaa cattaagcat gta                                          23

<210> SEQ ID NO 3
<211> LENGTH: 18
<212> TYPE: DNA
<213> ORGANISM: artificial sequence
<220> FEATURE:
<223> OTHER INFORMATION: 2-F primer

<400> SEQUENCE: 3
ttgtcggcat aacatggg                                                18

<210> SEQ ID NO 4
<211> LENGTH: 24
<212> TYPE: DNA
<213> ORGANISM: artificial sequence
<220> FEATURE:
<223> OTHER INFORMATION: 2-R primer

<400> SEQUENCE: 4
gttgtaagta tccactttaa gaaa                                         24

<210> SEQ ID NO 5
<211> LENGTH: 20
<212> TYPE: DNA
<213> ORGANISM: artificial sequence
<220> FEATURE:
<223> OTHER INFORMATION: 3-F primer

<400> SEQUENCE: 5
aaggctcaat tgtacttcat                                              20

<210> SEQ ID NO 6
<211> LENGTH: 22
<212> TYPE: DNA
<213> ORGANISM: artificial sequence
<220> FEATURE:
<223> OTHER INFORMATION: 3-R primer

<400> SEQUENCE: 6
tcaacacaga aagaactaaa cc                                           22

<210> SEQ ID NO 7
<211> LENGTH: 21
<212> TYPE: DNA
<213> ORGANISM: artificial sequence
<220> FEATURE:
<223> OTHER INFORMATION: 4-F primer

<400> SEQUENCE: 7
cagccaattt cttttgttac t                                            21
```

<210> SEQ ID NO 8
<211> LENGTH: 20
<212> TYPE: DNA
<213> ORGANISM: artificial sequence
<220> FEATURE:
<223> OTHER INFORMATION: 4-R primer

<400> SEQUENCE: 8
tgctctgaaa aagaacatgg                                               20

<210> SEQ ID NO 9
<211> LENGTH: 20
<212> TYPE: DNA
<213> ORGANISM: artificial sequence
<220> FEATURE:
<223> OTHER INFORMATION: 5-F primer

<400> SEQUENCE: 9
acatctgatt ctggacagtt                                               20

<210> SEQ ID NO 10
<211> LENGTH: 21
<212> TYPE: DNA
<213> ORGANISM: artificial sequence
<220> FEATURE:
<223> OTHER INFORMATION: 5-R primer

<400> SEQUENCE: 10
agaccttttt tgtaccaccc t                                             21

<210> SEQ ID NO 11
<211> LENGTH: 22
<212> TYPE: DNA
<213> ORGANISM: artificial sequence
<220> FEATURE:
<223> OTHER INFORMATION: 6-F primer

<400> SEQUENCE: 11
atttctgaag aggctctaca gt                                            22

<210> SEQ ID NO 12
<211> LENGTH: 20
<212> TYPE: DNA
<213> ORGANISM: artificial sequence
<220> FEATURE:
<223> OTHER INFORMATION: 6-R primer

<400> SEQUENCE: 12
ctagaaatgg cttggaagtt                                               20

<210> SEQ ID NO 13
<211> LENGTH: 20
<212> TYPE: DNA
<213> ORGANISM: artificial sequence
<220> FEATURE:
<223> OTHER INFORMATION: 7-F primer

<400> SEQUENCE: 13
ctcatgcgct tactaaggtt                                               20

<210> SEQ ID NO 14
<211> LENGTH: 21
<212> TYPE: DNA
<213> ORGANISM: artificial sequence
<220> FEATURE:
<223> OTHER INFORMATION: 7-R primer

```
<400> SEQUENCE: 14
catcgatgta atctgggatt a                                             21

<210> SEQ ID NO 15
<211> LENGTH: 22
<212> TYPE: DNA
<213> ORGANISM: artificial sequence
<220> FEATURE:
<223> OTHER INFORMATION: 8-F primer

<400> SEQUENCE: 15
cctagaaaac ctaccgttag tg                                            22

<210> SEQ ID NO 16
<211> LENGTH: 20
<212> TYPE: DNA
<213> ORGANISM: artificial sequence
<220> FEATURE:
<223> OTHER INFORMATION: 8-R primer

<400> SEQUENCE: 16
agctccaact cttggacagc                                               20

<210> SEQ ID NO 17
<211> LENGTH: 22
<212> TYPE: DNA
<213> ORGANISM: artificial sequence
<220> FEATURE:
<223> OTHER INFORMATION: 9-F primer

<400> SEQUENCE: 17
gatatgtttg taatggtaac tc                                            22

<210> SEQ ID NO 18
<211> LENGTH: 21
<212> TYPE: DNA
<213> ORGANISM: artificial sequence
<220> FEATURE:
<223> OTHER INFORMATION: 9-R primer

<400> SEQUENCE: 18
agcatagcta aaaggcaatg c                                             21

<210> SEQ ID NO 19
<211> LENGTH: 22
<212> TYPE: DNA
<213> ORGANISM: artificial sequence
<220> FEATURE:
<223> OTHER INFORMATION: 10-F primer

<400> SEQUENCE: 19
cgcaaagact gaacccacta ac                                            22

<210> SEQ ID NO 20
<211> LENGTH: 24
<212> TYPE: DNA
<213> ORGANISM: artificial sequence
<220> FEATURE:
<223> OTHER INFORMATION: 10-R primer

<400> SEQUENCE: 20
ttgcctctgt tgttacttgg agat                                          24
```